(12) United States Patent
Bell et al.

(10) Patent No.: US 8,993,588 B2
(45) Date of Patent: Mar. 31, 2015

(54) CARBOXAMIDE HETEROCYCLIC CGRP RECEPTOR ANTAGONISTS

(75) Inventors: Ian Bell, Harleysville, PA (US); Harold Selnick, Ambler, PA (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 898 days.

(21) Appl. No.: 12/602,676

(22) PCT Filed: Jun. 2, 2008

(86) PCT No.: PCT/US2008/006958
§ 371 (c)(1),
(2), (4) Date: Dec. 2, 2009

(87) PCT Pub. No.: WO2008/153849
PCT Pub. Date: Dec. 18, 2008

(65) Prior Publication Data
US 2010/0179166 A1    Jul. 15, 2010

Related U.S. Application Data

(60) Provisional application No. 60/933,212, filed on Jun. 5, 2007.

(51) Int. Cl.
*A61K 31/44* (2006.01)
*C07D 471/20* (2006.01)
*C07D 519/00* (2006.01)

(52) U.S. Cl.
CPC ............ *C07D 471/20* (2013.01); *C07D 519/00* (2013.01)
USPC ........................................... 514/287; 546/64

(58) Field of Classification Search
None
See application file for complete search history.

(56) References Cited

U.S. PATENT DOCUMENTS

| | | | |
|---|---|---|---|
| 7,189,722 B2 | 3/2007 | Bell et al. | |
| 7,192,954 B2 | 3/2007 | Bell et al. | |
| 7,202,251 B2 | 4/2007 | Bell et al. | |
| 7,205,293 B2 | 4/2007 | Bell et al. | |
| 7,390,798 B2 | 6/2008 | Williams et al. | |
| 7,591,795 B2 * | 9/2009 | Whalen et al. | 601/11 |
| 7,629,501 B2 * | 12/2009 | Labit et al. | 604/372 |
| 7,893,079 B2 * | 2/2011 | Wood et al. | 514/278 |
| 8,143,266 B2 * | 3/2012 | Bell et al. | 514/278 |
| 2007/0265225 A1 | 11/2007 | Wood et al. | |
| 2008/0004304 A1 | 1/2008 | Bell et al. | |
| 2008/0096878 A1 | 4/2008 | Bell et al. | |
| 2008/0214511 A1 | 9/2008 | Bell et al. | |
| 2009/0054408 A1 | 2/2009 | Bell et al. | |
| 2009/0105228 A1 | 4/2009 | Williams | |
| 2009/0221535 A1 | 9/2009 | Bell et al. | |
| 2009/0247514 A1 | 10/2009 | Bell et al. | |
| 2011/0306626 A1 * | 12/2011 | Selnick et al. | 514/278 |

FOREIGN PATENT DOCUMENTS

| | | | | |
|---|---|---|---|---|
| WO | 2006031513 A2 | 3/2006 | | |
| WO | 2006031610 A2 | 3/2006 | | |
| WO | 2007061677 A2 | 5/2007 | | |
| WO | 2008073251 A1 | 6/2008 | | |
| WO | 2008112159 A2 | 9/2008 | | |
| WO | 2008127584 A1 | 10/2008 | | |
| WO | 2008130512 A1 | 10/2008 | | |
| WO | 2008130524 | * 10/2008 | ............ | A61K 31/44 |
| WO | 2008130524 A1 | 10/2008 | | |
| WO | 2008153849 A2 | 12/2008 | | |
| WO | 2008153852 A1 | 12/2008 | | |
| WO | 2009105348 A1 | 8/2009 | | |
| WO | 2009120652 A2 | 10/2009 | | |
| WO | 2006031606 A2 | 5/2010 | | |

OTHER PUBLICATIONS

International Search Report for PCT/US08/06958, mailed Aug. 20, 2008.
Patani, G. A., et al., Bioisosterism, vol. 96, No. 8, 1996, p. 3147-3176.
Supplementary European Search Report and Opinion for counterpart European Application No. EP 08 76 8050 filed Jun. 2, 2008.

* cited by examiner

*Primary Examiner* — Noble Jarrell
(74) *Attorney, Agent, or Firm* — H. Eric Fischer; John C. Todaro

(57) ABSTRACT

Compounds of formula I:

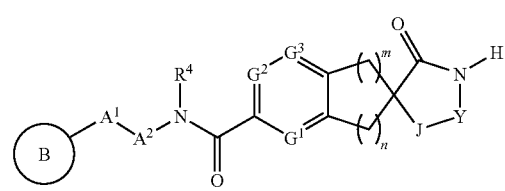

wherein variables $A^1$, $A^2$, B, m, n, J, $R^4$, $G^1$, $G^2$, $G^3$ and Y are as described herein, which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

14 Claims, No Drawings

CARBOXAMIDE HETEROCYCLIC CGRP RECEPTOR ANTAGONISTS

CROSS-REFERENCE TO RELATED APPLICATIONS

This application claims priority under 35 U.S.C. §119(e) of U.S. provisional application Ser. No. 60/933,212, filed Jun. 5, 2007.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), and salivary levels of CGRP were shown to be elevated in migraine subjects between attacks (Bellamy et al., Headache, 2006, 46, 24-33). CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196); tooth pain (Awawdeh et al., Int. Endocrin. J., 2002, 35, 30-36); non-insulin dependent diabetes mellitus (Molina et al., Diabetes, 1990, 39, 260-265); vascular disorders; inflammation (Zhang et al., Pain, 2001, 89, 265); arthritis, bronchial hyperreactivity, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.); neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of formula I:

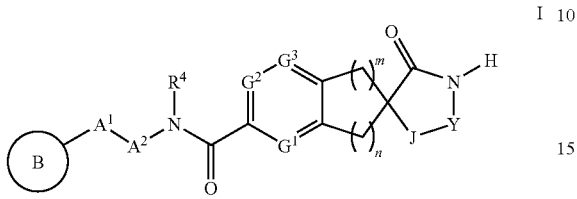

wherein variables $A^1$, $A^2$, B, m, n, J, $R^4$, $G^1$, $G^2$, $G^3$ and Y are as described herein, which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

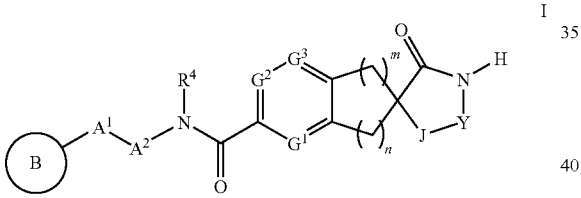

wherein:

B is selected from the group consisting of $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuryl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isoxazolyl, isoxazolinyl, isoxazolidinyl, morpholinyl, naphthyridinyl, oxazolyl, oxazolinyl, oxazolidinyl, oxazepanyl, oxadiazolyl, 2-oxoazepinyl, 4-oxonaphthyridinyl, 2-oxopiperazinyl, 2-oxopiperidinyl, 2-oxopyrrolidinyl, 2-oxopyridinyl, 2-oxoquinolinyl, 2-oxobenzimidazolyl, phthalazinyl, piperidinyl, piperazinyl, pyrazinyl, pyrazolidinyl, pyrazolyl, pyridazinyl, pyridyl, pyrimidinyl, pyrimidyl, pyrrolidinyl, quinazolinyl, quinolinyl, quinoxalinyl, tetrahydrofuryl, tetrahydropyranyl, tetrahydrothiopyranyl, tetrahydroimidazopyridinyl, tetrahydroisoquinolinyl, tetrahydroquinolinyl, tetrazolyl, thiamorpholinyl, thiamorpholinyl sulfoxide, thiazepinyl, thiazolyl, thiazolinyl, thiazolidinyl, thienyl, thienofuryl, thienothienyl, triazolinyl and triazolyl, wherein B is unsubstituted or substituted with 1-5 substituents each independently selected from $R^1$, $R^2$, $R^{3a}$ and $R^{3b}$;

$R^1$, $R^2$, $R^{3a}$ and $R^{3b}$ are independently selected from:
(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl,
    and wherein said phenyl or heterocycle is unsubstituted or substituted with 1-5 substituents each independently selected from
      (i) —$C_{1-6}$alkyl,
      (ii) —O—$C_{1-6}$alkyl,
      (iii) halo,
      (iv) hydroxy,
      (v) trifluoromethyl, and
      (vi) —$OCF_3$,
  (f) —$CO_2R^9$, wherein $R^9$ is selected from
    (i) hydrogen,
    (ii) —$C_{1-6}$alkyl which is unsubstituted or substituted with 1-6 fluoro,
    (iii) —$C_{5-6}$cycloalkyl,
    (iv) benzyl and
    (v) phenyl,
  (g) —$NR^{10}R^{11}$, wherein $R^{10}$ and $R^{11}$ are each independently selected from:
    (i) hydrogen,
    (ii) —$C_{1-6}$alkyl which is unsubstituted or substituted with 1-6 fluoro,
    (iii) —$C_{5-6}$cycloalkyl,
    (iv) benzyl,
    (v) phenyl,
    (vi) —$CO_2R^9$ and
    (vii) —$SO_2R^{12}$, wherein $R^{12}$ is selected from
      (I) —$C_{1-6}$alkyl which is unsubstituted or substituted with 1-6 fluoro,
      (II) —$C_{5-6}$cycloalkyl,
      (III) benzyl and
      (IV) phenyl,
  (h) —$SO_2R^{12}$,
  (i) —$CONR^{10a}R^{11a}$, wherein $R^{10a}$ and $R^{11a}$ are each independently selected from
    (i) hydrogen,
    (ii) —$C_{1-6}$alkyl which is unsubstituted or substituted with 1-6 fluoro,
    (iii) —$C_{5-6}$cycloalkyl,
    (iv) benzyl and
    (v) phenyl,
    or $R^{10a}$ and $R^{11a}$ are joined to form a ring selected from azetidinyl, pyrrolidinyl, piperidinyl, piperazinyl and morpholinyl, which ring is unsubstituted or substituted with 1-5 substituents each independently selected from
      (i) —$C_{1-6}$alkyl,
      (ii) —O—$C_{1-6}$alkyl,
      (iii) halo,
      (iv) hydroxyl,
      (v) phenyl and
      (vi) benzyl, (j) trifluoromethyl,
(k) —OCO$_2$R$^9$,
(l) —(NR$^{10a}$)CO$_2$R$^9$,
(m) —O(CO)NR$^{10a}$R$^{11a}$, and
(n) —(NR$^9$)(CO)NR$^{10a}$R$^{11a}$, (2) —C$_{3-6}$cycloalkyl, which is unsubstituted or substituted with 1-7 substituents each independently selected from
  (a) halo,
  (b) hydroxy,
  (c) —O—C$_{1-6}$alkyl,
  (d) trifluoromethyl and
  (e) phenyl, wherein the phenyl is unsubstituted or substituted with 1-5 substituents each independently selected from
    (i) —C$_{1-6}$alkyl,
    (ii) —O—C$_{1-6}$alkyl,
    (iii) halo,
    (iv) hydroxy and
    (v) trifluoromethyl, (3) phenyl or heterocycle, wherein the heterocycle is selected from pyridinyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, benzimidazolyl, benzopyranyl, benzofuryl, benzothiazolyl, benzoxazolyl, chromanyl, furyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, and wherein the phenyl or heterocycle is unsubstituted or substituted with 1-5 substituents each independently selected from:
  (a) —C$_{1-6}$alkyl which is unsubstituted or substituted with 1-6 fluoro,
  (b) halo,
  (c) hydroxy,
  (d) —O—C$_{1-6}$alkyl, which is unsubstituted or substituted with 1-6 fluoro,
  (e) —C$_{3-6}$cycloalkyl,
  (f) phenyl or heterocycle, wherein the heterocycle is selected from pyridinyl, pyrimidinyl, pyrazinyl, thienyl and morpholinyl,
    and wherein the phenyl or heterocycle is unsubstituted or substituted with 1-5 substituents each independently selected from
      (i) —C$_{1-6}$alkyl,
      (ii) —O—C$_{1-6}$alkyl,
      (iii) halo,
      (iv) hydroxy and
      (v) trifluoromethyl,
  (g) —CO$_2$R$^9$,
  (h) —NR$^{10}$R$^{11}$,
  (i) —CONR$^{10}$R$^{11}$,
  (j) —SO$_2$R$^{12}$, and
  (k) oxo,
(4) halo,
(5) oxo,
(6) hydroxy,
(7) —O—C$_{1-6}$alkyl, which is unsubstituted or substituted with 1-5 halo,
(8) —CN,
(9) —CO$_2$R$^9$,
(10) —NR$^{10}$R$^{11}$,
(11) —SO$_2$R$^{12}$,
(12) —CONR$^{10a}$R$^{11a}$,
(13) —OCO$_2$R$^9$,
(14) —(NR$^{10a}$)CO$_2$R$^9$,
(15) —O(CO)NR$^{10a}$R$^{11a}$,
(16) —(NR$^9$)(CO)NR$^{10a}$R$^{11a}$,
(17) —SO$_2$NR$^{10a}$R$^{11a}$,
(18) —SR$^{12}$,
(19) —S(O)R$^{12}$,
(20) —(NR$^9$)(CO)NR$^{10a}$R$^{11a}$,
(21) —(CO)—(CO)NR$^{10a}$R$^{11a}$, and
(22) —(CO)—(CO)OR$^9$;

or R$^{3a}$ and R$^{3b}$ and the atom(s) to which they are attached are joined to form a ring selected from azetidinyl, azepanyl, azepinyl, cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, thiadiazolyl, oxadiazolyl, isoxazolyl, pyrazolyl, triazolyl, pyridinyl, pyrimidinyl, pyrazinyl, pyridazinyl, triazinyl, pyrrolyl, pyrrolinyl, morpholinyl, azetidinyl, pyrrolidinyl, piperidinyl, tetrahydrofuranyl, tetrahydropyranyl, tetrahydropyridinyl, furanyl, dihydrofuranyl, dihydropyranyl, dihydrothienyl, tetrahydrothienyl, dihydrothiopyranyl, tetrahydrothiopyranyl, pyrrolidinyl, piperidinyl, and piperazinyl, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) hydroxy,
    (iii) —O—C$_{1-6}$alkyl, which is unsubstituted or substituted with 1-5 substituents each independently selected from
      (I) —O—C$_{1-6}$alkyl,
      (II) halo, and
      (III) hydroxy,
    (iv) —C$_{3-6}$cycloalkyl, which is unsubstituted or substituted with 1-5 substituents each independently selected from
      (I) —C$_{1-6}$alkyl,
      (II) —O—C$_{1-6}$alkyl,
      (III) halo,
      (IV) hydroxy,
      (V) trifluoromethyl and
      (VI) —OCF$_3$,
    (v) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from
      (I) —C$_{1-6}$alkyl,
      (II) —O—C$_{1-6}$alkyl,
      (III) halo,
      (IV) hydroxy,
      (V) trifluoromethyl and
      (VI) —OCF$_3$,
    (vi) —CO$_2$R$^9$,
    (vii) —NR$^{10}$R$^{11}$,
    (viii) —SO$_2$R$^{12}$,
    (ix) —CONR$^{10a}$R$^{11a}$, and
    (x) —(NR$^{10a}$)CO$_2$R$^9$,
  (b) —C$_{3-6}$cycloalkyl, which is unsubstituted or substituted with 1-5 substituents each independently selected from (i) halo,
(ii) hydroxy,
(iii) —O—$C_{1-6}$alkyl,
(iv) trifluoromethyl and
(v) phenyl,
(c) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
(i) halo,
(ii) hydroxy,
(iii) —$C_{3-6}$cycloalkyl,
(iv) —O—$C_{1-6}$alkyl which is unsubstituted or substituted with 1-6 fluoro, and
(v) —$C_{1-6}$alkyl which is unsubstituted or substituted with 1-6 fluoro,
(d) halo,
(e) —$SO_2R^{12}$,
(f) hydroxy,
(g) —O—$C_{1-6}$alkyl which is unsubstituted or substituted with 1-5 halo,
(h) —CN,
(i) —$COR^{12}$,
(j) —$NR^{10}R^{11}$,
(k) —$CONR^{10a}R^{11a}$,
(l) —$CO_2R^9$,
(m) —$(NR^{10a})CO_2R^9$,
(n) —$O(CO)NR^{10a}R^{11a}$,
(o) —$(NR^9)(CO)NR^{10a}R^{11a}$, and
(p) oxo;
$A^1$ and $A^2$ are each independently selected from:
(1) a bond,
(2) —$CR^{13}R^{14}$—, wherein $R^{13}$ and $R^{14}$ are independently selected from
(a) hydrogen,
(b) $C_{1-6}$ alkyl, which is unsubstituted or substituted with 1-5 substituents each independently selected from
(i) halo,
(ii) hydroxy,
(iii) —$NR^{10}R^{11}$,
(iv) —$CONR^{10a}R^{11a}$ and
(v) —$CO_2R^9$,
(c) phenyl, which is unsubstituted or substituted with 1-3 substituents each independently selected from
(i) $C_{1-4}$alkyl,
(ii) hydroxyl and
(iii) halo,
(d) —$CONR^{10}$—($C_{1-6}$alkyl)-$NR^{15}R^{16}$, wherein $R^{15}$ and $R^{16}$ are each independently selected from
(i) hydrogen,
(ii) —$C_{1-6}$alkyl,
(iii) —$COR^9$ and
(iv) —$CO_2R^9$,
(e) —$CO_2R^9$,
(f) —$CONR^{10a}R^{11a}$, and
(g) hydroxy,
(3) —$CH_2CR^{13}R^{14}$—, and
(4) —C(=O)—;
$G^1$, $G^2$ and $G^3$ are each independently selected from:
(1) —$C(R^5)$=,
(2) —N=, and
(3) —$(N^+$—$O^-)$=,
wherein no more than two of $G^1$, $G^2$ and $G^3$ are —$C(R^5)$=; or wherein 01 is selected from:

(1) —$C(R^5)$=,
(2) —N=, and
(3) —$(N^+$—$O^-)$=,
and -$G^2$=$G^3$- taken together are selected from:
(1) —S—,
(2) —O—,
(3) —$N(R^{10})$—;
J is independently selected from:
(1) =$C(R^{6a})$—,
(2) —$CR^{13}R^{14}$—,
(3) —C(=O)—, and
(4) —$N(R^{15})$—;
Y is independently selected from:
(1) =$C(R^{6b})$—,
(2) —$CR^{13}R^{14}$—,
(3) —C(=O)—,
(4) —$SO_2$—,
(5) =N—, and
(6) —$N(R^{6b})$—;
$R^4$ is selected from
(1) hydrogen,
(2) $C_{1-6}$ alkyl which is unsubstituted or substituted with 1-6 fluoro,
(3) $C_{5-6}$ cycloalkyl,
(4) benzyl and
(5) phenyl,
or $R^4$ is joined to B to form a ring selected from piperidinyl, pyrrolidinyl, piperazinyl, azetidinyl, azepinyl and morpholinyl, which ring is unsubstituted or substituted with 1-5 substituents each independently selected from
(1) —$C_{1-6}$alkyl,
(2) —O—$C_{1-6}$alkyl,
(3) halo,
(4) hydroxy,
(5) phenyl and
(6) benzyl;
$R^5$ is independently selected from:
(1) hydrogen,
(2) $C_{1-6}$alkyl,
(3) —O—$C_{1-6}$alkyl,
(4) —$OCF_3$,
(5) trifluoromethyl,
(6) halo,
(7) hydroxy, and
(8) —CN;
$R^{6a}$ and $R^{6b}$ are each independently selected from:
(1) hydrogen;
(2) —$C_{1-4}$alkyl, which is unsubstituted or substituted with 1-5 substituents each independently selected from:
(a) halo,
(b) —O—$C_{1-6}$alkyl,
(c) —$C_{3-6}$cycloalkyl,
(d) phenyl or heterocycle, wherein the heterocycle is selected from imidazolyl, oxazolyl, pyridinyl, pyrimidinyl, pyrazinyl, pyridazinyl, piperidinyl, piperazinyl, pyrrolidinyl, thiazolyl, thienyl, triazolyl, or morpholinyl, which phenyl or heterocycle is unsubstituted or substituted with 1-3 substituents each independently selected from
(i) —$C_{1-6}$alkyl,
(ii) —O—$C_{1-6}$alkyl,
(iii) halo,
(iv) hydroxy,
(v) trifluoromethyl and
(vi) —$OCF_3$,
(3) phenyl or heterocycle, wherein the heterocycle is selected from pyridinyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from
(a) —$C_{1-4}$-alkyl which is unsubstituted or substituted with 1-5 fluoro,
(b) halo,
(c) hydroxy,
(d) —O—$C_{1-4}$alkyl which is unsubstituted or substituted with 1-5 fluoro,
(e) —$C_{3-6}$cycloalkyl and
(f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$, or $R^{6a}$ and $R^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$alkyl,
(iv) —$C_{3-6}$cycloalkyl,
(v) phenyl or heterocycle, wherein the heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from
(I) —$C_{1-6}$alkyl,
(II) —O—$C_{1-6}$alkyl,
(III) halo,
(IV) hydroxy,
(V) trifluoromethyl and
(VI) —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$,
(b) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
(i) —$C_{1-6}$alkyl, which is unsubstituted or substituted with 1-6 fluoro,
(ii) —O—$C_{1-6}$alkyl, which is unsubstituted or substituted with 1-6 fluoro,
(iii) halo,
(iv) hydroxy, and
(v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
$R^{15}$ is selected from:
(1) hydrogen,
(2) —$C_{1-6}$alkyl or
(3) —$C_{3-6}$cycloalkyl, wherein the alkyl or cycloalkyl are unsubstituted or substituted with 1-7 substituents where the substituents are independently selected from:
(a) halo,
(b) hydroxy,
(c) —O—$C_{1-6}$alkyl,
(d) —$C_{3-6}$cycloalkyl,
(e) phenyl, which is unsubstituted or substituted with 1-5 substituents where the substituents are independently selected from:
(i) —$C_{1-6}$alkyl,
(ii) —O—$C_{1-6}$alkyl,
(iii) halo,
(iv) hydroxy, and
(v) trifluoromethyl,
(f) —$CO_2R^9$,
(g) —$NR^{10}R^{11}$,
(h) —$CONR^{10}R^{11}$,
(i) —$SO_2R^{12}$, and
(j) trifluoromethyl, and
(3) phenyl or heterocycle, wherein the heterocycle is selected from pyridyl, pyrimidinyl, pyrazinyl, thienyl, or morpholinyl, which is unsubstituted or substituted with 1-5 substituents where the substituents are independently selected from:
(a) —$C_{1-6}$alkyl,
(b) —O—$C_{1-6}$alkyl,
(c) halo,
(d) hydroxy, and
(e) trifluoromethyl;
m is 1 or 2;
n is 1 or 2;
and pharmaceutically acceptable salts thereof and individual enantiomers and diastereomers thereof.

The invention is also directed to medicaments or pharmaceutical compositions for treating diseases or disorders in which CGRP is involved, such as migraine, which comprise a compound of formula (I), or a pharmaceutically acceptable salt thereof, and a pharmaceutically acceptable carrier.

The invention is also directed to the use of a compound of formula (I) or a pharmaceutically acceptable salt thereof for treating diseases or disorders in which CGRP is involved, such as migraine.

The invention is further directed to the use of a compound of the invention or a pharmaceutically acceptable salt thereof, for the manufacture of a medicament or a composition for treating diseases or disorders in which CGRP is involved, such as migraine, by combining a compound of formula (I) with one or more pharmaceutically acceptable carriers.

In one embodiment of the present invention, B is phenyl. In another embodiment of the present invention, B is thienyl. In another embodiment of the present invention B, is pyridinyl. In another embodiment of the present invention B is isoquinolinyl. In another embodiment of the present invention, B is tetrahydroisoquinolinyl. In another embodiment of the present invention, B is naphthyl. In another embodiment of the present invention, B is isoxazolyl. In another embodiment of the present invention, B is indolyl. In another embodiment of the present invention, B is piperidinyl. In another embodiment of the present invention, B is tetrahydrofuryl. In another embodiment of the present invention, B is piperazinyl. In another embodiment of the present invention B is pyrazolyl. In another embodiment of the present invention, B is pyrrolidinyl, which is optionally substituted with oxo.

In an embodiment of the present invention $R^1$, $R^2$, $R^{3a}$ and $R^{3b}$ are independently selected from:
(1) $C_{1-6}$ alkyl, which is unsubstituted or substituted with 1-5 halo or hydroxy,
(2) $C_{3-6}$ cycloalkyl,
(3) —O—$C_{1-6}$alkyl,
(4) —$OCF_3$,
(5) trifluoromethyl,
(6) halo,
(7) oxo
(8) —CN,
(9) —$COR^{12}$,
(10) —$CO_2R^{12}$,
(11) —$CONR^{10a}R^{11a}$,
(12) —$NR^{10a}CO_2R^9$,
(13) phenyl, which is unsubstituted or substituted with 1-5 substituents each independently selected from: $C_{1-6}$alkyl, —O—$C_{1-6}$alkyl, halo, —OH and —$CF_3$,
(14) heterocycle selected from: pyridyl, pyrimidinyl, pyrazinyl, thienyl, pyrrolidinyl, piperidinyl or morpholinyl, which is unsubstituted or substituted with 1-5 substituents each independently selected from: $C_{1-6}$alkyl, —O—$C_{1-6}$alkyl, halo, —OH and —$CF_3$.

The radicals $R^1$, $R^2$, $R^{3a}$ and $R^{3b}$ may be substituted at any of the positions for the B ring where valency permits substitution. In some embodiments, each of $R^1$, $R^2$, $R^{3a}$ and $R^{3b}$ are substituted at different ring atoms. In one embodiment, the variables $R^{3a}$ and $R^{3b}$ are substituted on the same ring atom of the B radical. For example, $R^{3a}$ and $R^{3b}$ may be substituted on the same carbon ring atom and may form an optionally substituted heterocyclic group as described above.

In one embodiment, $R^1$ may be substituted on the same B atom that is linked to $A^1$ and $A^2$.

In an embodiment of the present invention $A^1$ is a bond and $A^2$ is —$CH_2$—. In another embodiment of the present invention, $A^1$ and $A^2$ are both $CR^{13}R^{14}$, and $R^{13}$ and $R^{14}$ are independently selected from
(a) hydrogen, and
(b) $C_{1-6}$ alkyl, which is unsubstituted or substituted with 1-5 halo or hydroxy.

In an embodiment of the present invention $A^1$ is —$CH_2$— or a bond, and $A^2$ is (C=O).

In an embodiment of the present invention J is selected from:
=$C(R^{6a})$—; —$CH_2$—; and —$N(R^{15})$—; wherein $R^{6a}$ and $R^{15}$ are defined herein. In another embodiment of the present invention J is —$CH_2$—. In another embodiment of the present invention J is —$N(R^{15})$—; wherein $R^{15}$ is defined herein. In yet another embodiment of the present invention J is =$C(R^{6a})$—; wherein $R^{6a}$ is defined herein.

In an embodiment of the present invention Y is selected from:
=$C(R^{6b})$—; —$CH_2$—; and —$C(=O)$—; wherein $R^{6b}$ is defined herein. In another embodiment of the present invention Y is —$CH_2$—. In another embodiment of the present invention Y is —$C(=O)$—. In yet another embodiment of the present invention Y is =$C(R^{6b})$— wherein $R^{6b}$ is defined herein.

In one embodiment, J is =$C(R^{6a})$— and Y is =$C(R^{6b})$—, wherein $R^{6a}$ and $R^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl, which is unsubstituted or substituted with 1-3 substituents each independently selected from:
  (i) halo,
  (ii) hydroxy,
  (iii) —O—$C_{1-6}$alkyl,
  (iv) —$C_{3-6}$cycloalkyl,
  (v) phenyl or heterocycle, wherein the heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from
    (I) —$C_{1-6}$alkyl,
    (II) —O—$C_{1-6}$alkyl,
    (III) halo,
    (IV) hydroxy,
    (V) trifluoromethyl and
    (VI) —$OCF_3$,
  (vi) —$CO_2R^9$,
  (vii) —$NR^{10}R^{11}$,
  (viii) —$SO_2R^{12}$,
  (ix) —$CONR^{10a}R^{11a}$, and
  (x) —$(NR^{10a})CO_2R^9$,
(b) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
  (i) —$C_{1-6}$alkyl, which is unsubstituted or substituted with 1-6 fluoro,
  (ii) —O—$C_{1-6}$alkyl, which is unsubstituted or substituted with 1-6 fluoro,
  (iii) halo,
  (iv) hydroxy, and
  (v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo.

In one embodiment, J is =C($R^{6a}$)— and Y is =C($R^{6b}$)—, wherein $R^{6a}$ and $R^{6b}$ and the atom(s) to which they are attached are joined to form an unsubstituted pyridinyl ring.

In an embodiment of the present invention $R^4$ is hydrogen.

In an embodiment of the present invention $G^1$, $G^2$ and $G^3$ are each independently selected from: —C($R^5$)= and —N=; wherein no more than two of $G^1$, $G^2$ and $G^3$ are selected to be —C($R^5$)=; and $R^5$ is defined herein.

In another embodiment of the present invention $G^1$ is selected from —C($R^5$)= and —N=; and -$G^2$=$G^3$- taken together are selected from: —S— and N($R^{10}$)—; wherein $R^5$ and $R^{10}$ are defined herein.

In yet another embodiment of the present invention one of $G^1$, $G^2$ and $G^3$ is —N= and the remaining two of $G^1$, $G^2$ and $G^3$ are —C(H)=. For example, $G^1$ and $G^3$ may be —C(H)= and $G^2$ is N=.

In an embodiment of the present invention $R^{15}$ is selected from:
(1) hydrogen,
(2) —$C_{1-4}$alkyl which is unsubstituted or substituted with 1-3 substituents each independently selected from: halo and phenyl.

In an embodiment of the present invention $R^{15}$ is hydrogen or methyl.

In an embodiment of the present invention $R^{15}$ is methyl.

In an embodiment of the present invention m is 1. In an embodiment of the present invention n is 1. In an embodiment of the present invention n is 2.

In one embodiment, the invention is directed to a sub-genus of compounds of formula (II):

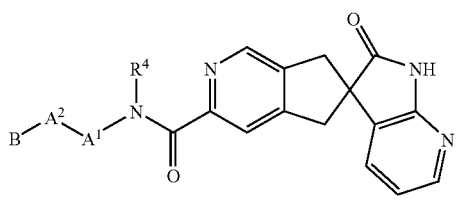

wherein variables $A^1$, $A^2$, B and $R^4$ are as described above herein, and pharmaceutically acceptable salts thereof. The invention is also directed to pharmaceutical compositions comprising the compounds of formula (II), and the use of the compounds of formula (II) and compositions in the prevention or treatment of such diseases in which CGRP is involved.

The invention is also directed to medicaments or pharmaceutical compositions for treating diseases or disorders in which CGRP is involved, such as migraine, which comprise a compound of formula (II), or a pharmaceutically acceptable salt thereof, and a pharmaceutically acceptable carrier.

The invention is also directed to a compound of formula (II) or a pharmaceutically acceptable salt thereof for use in medicine, e.g. for treating diseases or disorders in which CGRP is involved, such as migraine.

The invention is further directed to the use of a compound of the invention or a pharmaceutically acceptable salt thereof for the manufacture of a medicament or a composition for treating diseases or disorders in which CGRP is involved, such as migraine, by combining a compound of formula (II) with one or more pharmaceutically acceptable carriers.

In one embodiment of the compounds of formula (II), B is phenyl. In another embodiment, B is thienyl. In another embodiment, B is pyridinyl. In another embodiment, B is isoquinolinyl. In another embodiment, B is tetrahydroisoquinolinyl. In another embodiment, B is naphthyl. In another embodiment, B is isoxazolyl. In another embodiment, B is indolyl. In another embodiment, B is piperidinyl. In another embodiment, B is tetrahydrofuryl. In another embodiment, B is piperazinyl. In another embodiment, B is pyrazolyl. In another embodiment, B is pyrrolidinyl, which is optionally substituted with oxo.

In an embodiment of the compounds of formula (II), $R^1$, $R^2$, $R^{3a}$ and $R^{3b}$ are independently selected from:
(1) $C_{1-6}$ alkyl, which is unsubstituted or substituted with 1-5 halo or hydroxy,
(2) $C_{3-6}$ cycloalkyl,
(3) —O—$C_{1-6}$alkyl,
(4) —$OCF_3$,
(5) trifluoromethyl,
(6) halo,
(7) oxo
(8) —CN,
(9) —$COR^{12}$,
(10) —$CO_2R^{12}$,
(11) —$CONR^{10a}R^{11a}$,
(12) —$NR^{10a}CO_2R^9$,
(13) phenyl, which is unsubstituted or substituted with 1-5 substituents each independently selected from: $C_{1-6}$alkyl, —O—$C_{1-6}$alkyl, halo, —OH and —$CF_3$,
(14) heterocycle selected from: pyridyl, pyrimidinyl, pyrazinyl, thienyl, pyrrolidinyl, piperidinyl or morpholinyl, which is unsubstituted or substituted with 1-5 substituents each independently selected from: $C_{1-6}$alkyl, —O—$C_{1-6}$alkyl, halo, —OH and —$CF_3$.

In an embodiment of compounds of formula (II), $A^1$ is a bond and $A^2$ is —$CH_2$—.

In another embodiment of the present invention, $A^1$ and $A^2$ are both $CR^{13}R^{14}$, and $R^{13}$ and $R^{14}$ are independently selected from
(a) hydrogen, and
(b) $C_{1-6}$ alkyl, which is unsubstituted or substituted with 1-5 halo or hydroxy.

In an embodiment of the compounds of formula (II), $A^1$ is —$CH_2$— or a bond, and $A^2$ is (C=O).

In an embodiment of the compounds of formula (II), $R^4$ is hydrogen.

Specific embodiments of compounds of formula (I) and (II) are described herein as Examples 1-42.

It is to be understood that where one or more of the above recited structures or substructures recite multiple substituents having the same designation each such variable may be the same or different from each similarly designated variable. For example, $R^9$ is recited multiple times in certain configurations of formula I, and each instance of $R^9$ in formula I may independently be any of the substructures defined under $R^9$. The invention is not limited to structures and substructures wherein each $R^9$ must be the same for a given structural configuration. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

The present invention includes compounds of formula I and II wherein on or more hydrogen atoms are replaced by deuterium.

Tautomers of compounds defined in Formula I and II are also included within the scope of the present invention. For example, compounds including carbonyl $CH_2C(O)$— groups (keto forms) may undergo tautomerism to form hydroxyl —CH=C(OH)— groups (enol forms). Both keto and enol forms are included within the scope of the present invention.

As appreciated by those of skill in the art, halo or halogen as used herein are intended to include chloro, fluoro, bromo and iodo.

As used herein, "alkyl" is intended to mean linear or branched structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclic group as defined herein is substituted, the substituent may be bonded to a ring carbon atom of the heterocyclic group, or on a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

The term "alkoxy," as in $C_1$-$C_6$ alkoxy, includes alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) Eur. J. Pharmacol. 415, 39-44). Briefly, membranes (25 μg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 μL) was added and the radioactivity was counted on a Topcount (Packard Instrument). Data analysis was carried out by using Prism and the $K_i$ was determined by using the Cheng-Prusoff equation (Cheng & Prusoff (1973) Biochem. Pharmacol. 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 μg/mL streptomycin, and maintained at 37° C. and 95% humidity. Cells were subcultured by treatment with 0.25% trypsin with 0.1% EDTA in HBSS. Stable cell line generation was accomplished by co-transfecting 10 μg of DNA with 30 μg Lipofectamine 2000 (Invitrogen) in 75 cm$^2$ flasks. CL receptor and RAMP 1 expression constructs were co-transfected in equal amounts. Twenty-four hours after transfection the cells were diluted and selective medium (growth medium+300 μg/mL hygromycin and 1 μg/mL puromycin) was added the following day. A clonal cell line was generated by single cell deposition utilizing a FACS Vantage SE (Becton Dickinson). Growth medium was adjusted to 150 μg/mL hygromycin and 0.5 μg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 μg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH}}$$

Where Y is observed CPM bound, $Y_{max}$ is total bound counts, $Y_{min}$ is non specific bound counts, ($Y_{max}-Y_{min}$) is specific bound counts, % $I_{max}$ is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare).

Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention may be used in combination with one or more other drugs in the treatment, prevention, control, amelioration, or reduction of risk of diseases or conditions for which compounds of Formula I or II or the other drugs may have utility, where the combination of the drugs together are safer or more effective than either drug alone. Such other drug(s) may be administered, by a route and in an amount commonly used therefor, contemporaneously or sequentially with a compound of Formula I or II. When a compound of Formula I or II is used contemporaneously with one or more other drugs, a pharmaceutical composition in unit dosage form containing such other drugs and the compound of Formula I or II is preferred. However, the combination therapy may also include therapies in which the compound of Formula I or II and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I or II.

For example, the present compounds may be used in conjunction with an an anti-migraine agent, such as ergotamine and dihydroergotamine, or other serotonin agonists, especially a $5\text{-}HT_{1B/1D}$ agonist, for example sumatriptan, naratriptan, zolmitriptan, eletriptan, almotriptan, frovatriptan, donitriptan, and rizatriptan, a $5\text{-}HT_{1D}$ agonist such as PNU-142633 and a $5\text{-}HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α- ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of a representative heterocyclic acid intermediate is illustrated in Scheme 1. Related intermediates bearing a variety of substituents may be prepared by employing appropriately substituted starting materials or by derivatization of any intermediates and/or final products as desired by methods known in the art. The known pyridine diester 1 [Hashimoto et al. (1997) *Heterocycles* 46, 581] may be reduced to the corresponding diol 2 with lithium borohydride. This diol can be converted to the dibromide 3 by reaction with phosphorus tribromide in THF. 7-Azaindole (4) may be protected with a variety of protecting groups, such as the 2-(trimethylsilyl)ethoxymethyl group shown in Scheme 1. Following the method of Marfat and Carter [(1987) *Tetrahedron Lett.* 28, 4027], treatment of 5 with pyridine hydrobromide perbromide provides the dibromoazaoxindole 6, which may be reduced to the corresponding azaoxindole 7 by reaction with zinc. The key alkylation of 7 with dibromide 3 may be carried out using cesium carbonate in DMF to afford the spiroazaoxindole 8. A variety of other bases and solvents may be employed in this alkylation reaction, and use of a different alkylating agent than the dibromide shown here can lead to other products. Treatment of compound 8 with aqueous HCl at reflux effects simultaneous hydrolysis of the nitrile and deprotection of the azaoxindole, affording the key acid intermediate 9. The methodology shown in Scheme 1 is not limited to azaoxindoles such as 7, but may be applied to a variety of suitably protected heterocyclic systems to give the corresponding spiro compounds.

SCHEME 1

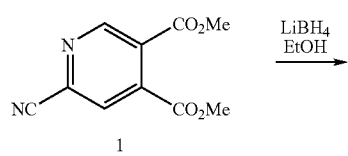

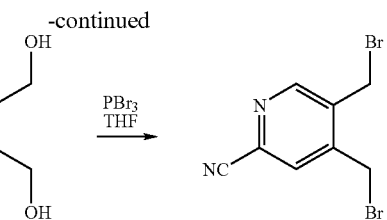

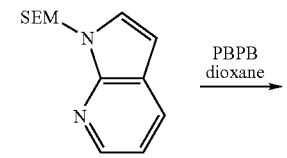

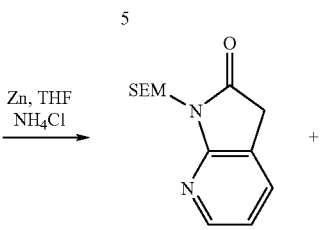

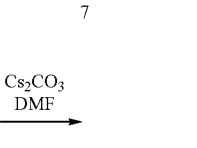

Key carboxylic acid intermediates, such as compound 9 in Scheme 1, may be resolved to give pure enantiomers using techniques familiar to those skilled in the art. For example, chromatography of the suitable intermediates on a chiral column can be used to provide the individual stereoisomers. Resolution may also be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

Key carboxylic acid intermediates may be further elaborated by techniques familiar to one skilled in the art to provide the final amide products, as shown in Scheme 2.

SCHEME 2

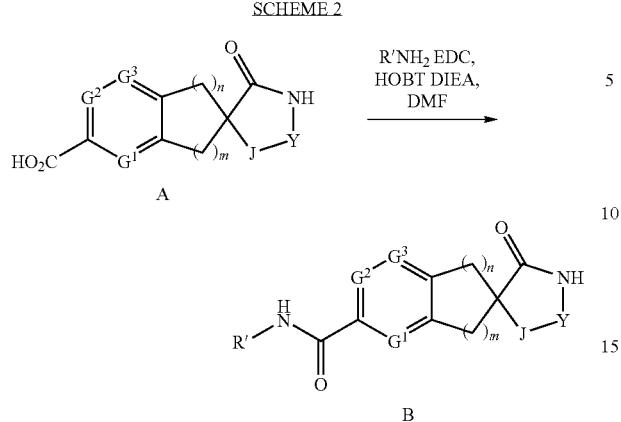

Thus, acid A may be coupled to an amine, R'NH$_2$, under standard EDC-HOBT coupling conditions to provide amide B. Other standard coupling conditions may be employed in the synthesis of such amides, such as use of an alternative coupling reagent like PyBOP, or activation of the carboxylic acid as an acid anhydride or acid chloride.

Most of the amines (R'NH$_2$) used to make the compounds of the present invention are readily available. They may be obtained from commercial sources or synthesized by methodology familiar to those skilled in the art and as described in the chemical literature.

Some of the amine intermediates can be prepared as outlined in Schemes 3 & 4. As shown in Scheme 3, addition of nitromethane to the known glutamic acid derived aldehyde 15 (*Tetrahedron Asymmetry* 1998, 3381-3394), followed by in situ elimination affords nitro olefin 16. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 18. Ring closure under standard conditions, followed by removal of a single tert-butoxycarbonyl group furnishes the lactam 20. Intermediates such as 18 can be further processed as in Scheme 4.

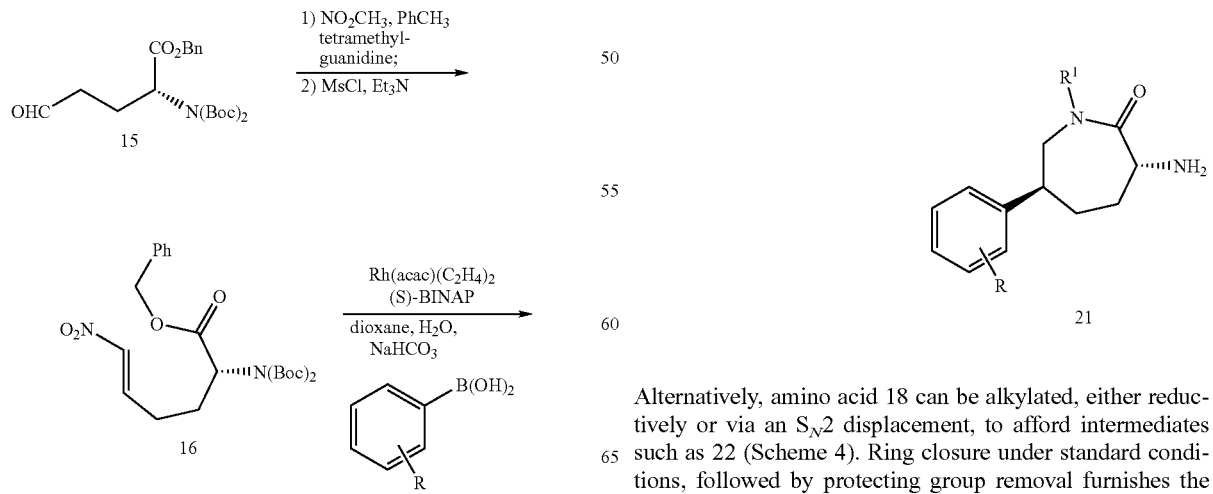

Alternatively, amino acid 18 can be alkylated, either reductively or via an S$_N$2 displacement, to afford intermediates such as 22 (Scheme 4). Ring closure under standard conditions, followed by protecting group removal furnishes the lactam 24.

SCHEME 4

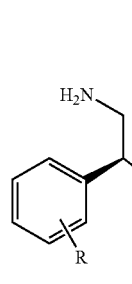

18

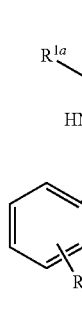

22

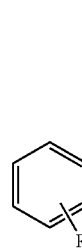

23

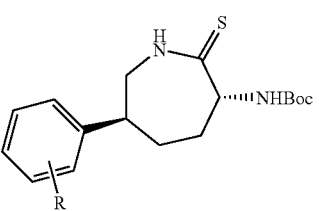

25

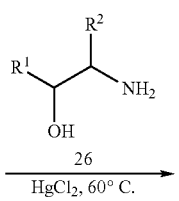

26

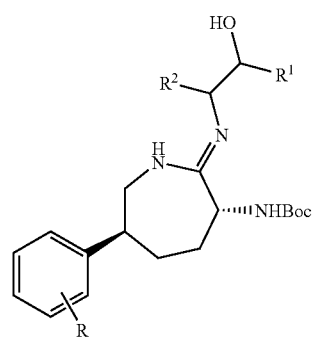

27

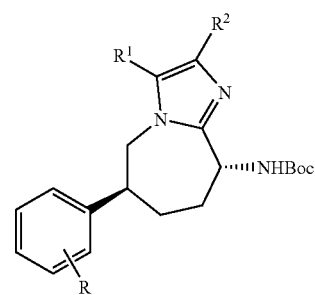

28

Fused imidazoles are prepared as shown in Scheme 5. Thioamide 25 is reacted with a variety of amino alcohols 26 in the presence of mercury (II) chloride to give amidines 27. Oxidation of the alcohol with concommitant ring closure using either the Dess-Martin periodinane or pyridinium dichromate finally yields imidazoles of the general formula 28.

Triazole derivatives are prepared as shown in Scheme 6. Addition of hydrazine to thioamide 25 gives the corresponding hydrazide 29. Various carboxylic acids or acid chlorides can undergo couplings under standard conditions affording after ring closure the desired fused triazoles 30.

SCHEME 5

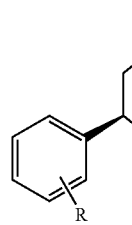

20

SCHEME 6

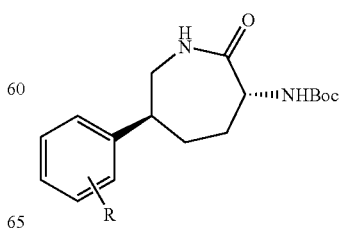

20

-continued

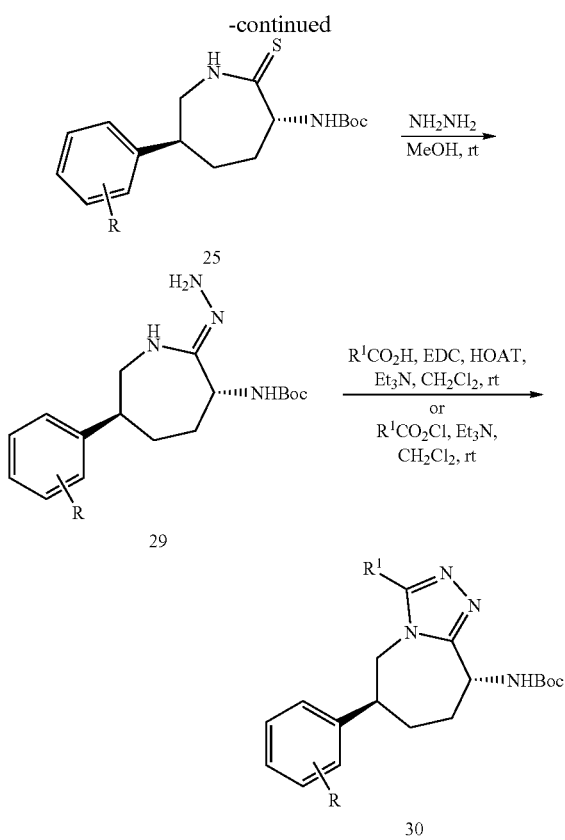

In some cases the final product B (Scheme 2) may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products.

The following examples are provided so that the invention might be more fully understood. These examples are illustrative only and should not be construed as limiting the invention in any way.

INTERMEDIATE 1

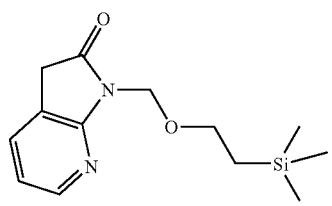 [SMILES: C[Si](C)(C)CCOCN1C(=O)Cc2cccnc21]

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL) The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

INTERMEDIATE 2

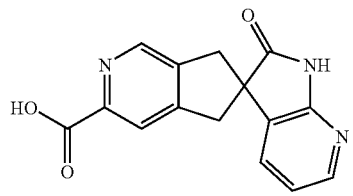 [SMILES: O=C(O)c1cc2c(cn1)CC1(C2)C(=O)Nc2ncccc21]

(±)-2'-Oxo-1',2',5,7-tetrahydrospiro[cyclopenta[c] pyridine-6,3'-pyrrolo[2,3-b]pyridine]-3-carboxylic acid hydrochloride Step A.
4,5-Bis(hydroxymethyl)pyridine-2-carbonitrile To a solution of dimethyl 6-cyanopyridine-3,4-dicarboxylate (2.00 g, 9.08 mmol) [Hashimoto et al. (1997) *Heterocycles* 46, 581] in EtOH (50 mL) was added lithium borohydride (4.54 mL of a 2 M solution in THF, 9.08 mmol) dropwise. The reaction mixture was stirred at ambient temperature for 3 h, and then cooled to 0° C. Saturated aqueous NaHCO$_3$ (20 mL) was added slowly and the quenched mixture was extracted with EtOAc (9×100 mL). The combined organic extracts were dried over Na$_2$SO$_4$, filtered, and concentrated in vacuo. The crude product was purified by silica gel chromatography, eluting with a gradient of CH$_2$Cl$_2$:MeOH—100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) dropwise. The reaction mixture was stirred at ambient temperature for 2 h, and then cooled to 0° C. Saturated aqueous NaHCO$_3$ (5 mL) was added slowly and the quenched mixture was extracted with CHCl$_3$ (2×30 mL). The combined organic extracts were dried over Na$_2$SO$_4$, filtered, and concentrated in vacuo. The crude product was purified by silica gel chromatography, eluting with a gradient of hexane:EtOAc—100:0 to 27:75, to give the title compound. MS: m/z=291 (M+1).

Step C. (±)-2'-Oxo-1'-{[2-(trimethylsilyl)ethoxy]methyl}-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (729 mg, 2.52 mmol) and 1-{[2-(trimethylsilyl)ethoxy]methyl}-1,3-dihydro-2H-pyrrolo[2,3-b]pyridin-2-one (665 mg, 2.52 mmol, described in Intermediate 1) in DMF (75 mL) was added cesium carbonate (2.46 g, 7.55 mmol), portionwise, over 5 min. After 2 h, acetic acid (0.15 mL) was added and the mixture was concentrated to a volume of about 25 mL, then partitioned between CHCl$_3$ (100 mL), saturated aqueous NaHCO$_3$ (30 mL) and brine (50 mL). The organic layer was removed and the aqueous layer was extracted further with CHCl$_3$ (100 mL). The combined organic extracts were dried over Na$_2$SO$_4$, filtered, and concentrated in vacuo. The crude product was purified by silica gel chromatography, eluting with a gradient of hexane:EtOAc—100:0 to 0:100, to give the title compound. MS: m/z=393 (M+1).

Step D. (±)-2'-Oxo-1',2',5,7-tetrahydrospiro[cyclopenta[c]pyridine-6,3'-pyrrolo[2,3-b]pyridine]-3-carboxylic acid hydrochloride To a solution of (±)-2'-oxo-1'-{[2-(trimethylsilyl)ethoxy]methyl}-1',2',5,7-tetrahydrospiro[cyclopenta[c]pyridine-6,3'-pyrrolo[2,3-b]pyridine]-3-carbonitrile from Step C (6.10 g, 15.5 mmol) in THF (30 mL) was added 3 N aqueous HCl (360 mL). The mixture was heated at reflux for 18 h, allowed to cool and concentrated to dryness in vacuo. The residue was redissolved in 3 N aqueous HCl (360 mL) and heated at reflux for 18 h. The cooled mixture was concentrated to dryness in vacuo to afford the title compound in sufficient purity for use in subsequent steps. MS: m/z=282 (M+1).

INTERMEDIATE 4

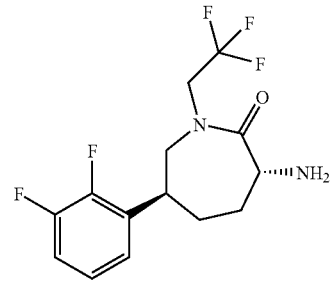 [SMILES: N[C@@H]1CC[C@@H](c2cccc(F)c2F)CN(CC(F)(F)F)C1=O]

(3R,6S)-3-Amino-6-(2,3-difluorophenyl)-1-(2,2,2-trifluoroethyl)azepan-2-one

Step A. 1-Benzyl 5-methyl N,N-bis(tert-butoxycarbonyl)-D-glutamate

To a solution of Boc-D-Glu-OBn (50.0 g, 148 mmol) in CH$_2$Cl$_2$ (400 mL) and MeOH (100 mL) at 0° C. was added (trimethylsilyl)diazomethane (2.0 M in hexanes, 89 mL, 118 mmol) dropwise via an addition funnel. After 1 h the reaction was concentrated under reduced pressure. This residue was diluted with CH$_3$CN (400 mL) and di-tert-butyl dicarbonate (48.5 g, 222 mmol) was added, followed by DMAP (18.1 g, 14.8 mmol). The mixture was stirred at ambient temperature for 24 h, then concentrated in vacuo. The crude product was purified by silica gel chromatography, eluting with a gradient of hexane:EtOAc—90:10 to 40:60, to give the title compound. MS: m/z=252 (M-C$_{10}$H$_{15}$O$_4$).

Step B. Benzyl (2R,5E)-2-[bis(tert-butoxycarbonyl)amino]-6-nitrohex-5-enoate

To a stirred solution of 1-benzyl 5-methyl N,N-bis(tert-butoxycarbonyl)-D-glutamate from Step A (48.2 g, 106.8 mmol) in Et$_2$O (400 mL), at −78° C., was added DIBAL (1.0 M in toluene, 133 mL, 133 mmol) slowly so as not to let the internal temperature exceed −65° C. After 15 min, an additional portion of DIBAL (20 mL, 20 mmol) was added. After stirring for a further 20 min, H$_2$O (300 mL) was added and the reaction was warmed to ambient temperature and stirred for 30 min. This mixture was diluted with Et$_2$O and H$_2$O, the layers separated and the aqueous phase extracted with more Et$_2$O. The combined organic extracts were washed with saturated aqueous sodium potassium tartrate (2×), then brine, then dried over MgSO$_4$, filtered and concentrated in vacuo to give benzyl N,N-bis(tert-butoxycarbonyl)-5-oxo-D-norvalinate. This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, and methanesulfonyl chloride (12.2 mL, 158 mmol) was added, followed by triethylamine (22.0 mL, 158 mmol) at 0° C. and the reaction mixture was allowed to warm to ambient temperature. After 1 h, additional methanesulfonyl chloride (3 mL, 39 mmol) and triethylamine (5.5 mL, 39 mmol) were added. The mixture was stirred for an additional 30 min, then diluted with Et$_2$O and aqueous NaHCO$_3$. The phases were separated and the aqueous layer was extracted further with Et$_2$O. The combined organic extracts were dried over MgSO$_4$, filtered and concentrated in vacuo. The crude product was purified by silica gel chromatography, eluting with a gradient of hexane:EtOAc—95:5 to 50:50, to give the title compound. MS: m/z=487 (M+Na).

Step C. Benzyl (5S)-N,N-bis(tert-butoxycarbonyl)-5-(2,3-difluorophenyl)-6-nitro-D-norleucinate A solution of benzyl (2R,5E)-2-[bis(tert-butoxycarbonyl)amino]-6-nitrohex-5-enoate from Step B (34.0 g, 73.2 mmol), 2,3-difluorophenylboronic acid (28.9 g, 183 mmol) and water (4.62 mL, 256 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at ambient temperature for 2 min then heated to 35° C. After 4 h, (S)-BINAP (255 mg, 0.41 mmol) and acetylacetanotobis(ethylene)rhodium(I) (94 mg, 0.36 mmol) were added. After an additional 2 h, the reaction was partitioned between CH$_2$Cl$_2$ and aqueous NaHCO$_3$. The aqueous layer was extracted with another portion of CH$_2$Cl$_2$. The combined organic extracts were dried over MgSO$_4$, filtered and concentrated in vacuo. The crude product was purified by silica gel chromatography, eluting with a gradient of hexane:EtOAc—95:5 to 40:60, to give the title compound. MS: m/z=379 (M-C$_{10}$H$_{15}$O$_4$)

Step D. (5S)-N$^2$,N$^2$-Bis(tert-butoxycarbonyl)-5-(2,3-difluorophenyl)-D-lysine A mixture of benzyl (5S)—N$^2$,N$^2$-bis(tert-butoxycarbonyl)-5-(2,3-difluorophenyl)-6-nitro-D-norleucinate from Step C (15.5 g, 26.8 mmol) and 10% Pd/C (12.0 g) in EtOH (175 mL), was hydrogenated at 55 psi for 18 h. An additional portion of 10% Pd/C (4.0 g) was added and the reaction mixture was hydrogenated at 55 psi for a further 18 h. The reaction mixture was filtered through Celite, washing with EtOH, and the filtrate was concentrated in vacuo to afford the title compound. MS: m/z=459 (M+1).

Step E. tert-Butyl (3R,6S)-6-(2,3-difluorophenyl)-2-oxoazepan-3-ylcarbamate

To a solution (5S)—N$^2$,N$^2$-bis(tert-butoxycarbonyl)-5-(2,3-difluorophenyl)-D-lysine from Step D (22.0 g, 48.0 mmol) in CH$_2$Cl$_2$ (700 mL) were added EDC (11.0 g, 57.6 mmol) and HOAT (3.27 g, 24.0 mmol) followed by triethylamine (10.0 mL, 72.0 mmol). After 1 h, aqueous NaHCO$_3$ was added, the layers were separated, and the aqueous phase was extracted with CH$_2$Cl$_2$. The combined organic extracts were dried over MgSO$_4$, filtered and concentrated in vacuo. The residue was purified by silica gel chromatography, eluting with CH$_2$Cl$_2$:MeOH—90:10, to give the title compound. MS: m/z=341 (M+1).

Step F: tert-Butyl (3R,6S)-6-(2,3-difluorophenyl)-2-oxo-1-(2,2,2-trifluoroethyl)azepan-3-ylcarbamate Sodium hydride (60% dispersion in mineral oil, 70.7 mg, 1.06 mmol) was added to a solution of tert-butyl (3R,6S)-6-(2,3-difluorophenyl)-2-oxoazepan-3-ylcarbamate from Step E (301 mg, 0.884 mmol) in DMF (7 mL) at −35° C.: After 15 min, 2,2,2-trifluoroethyl trichloromethanesulfonate (0.314 mL, 1.91 mmol) was added and stirring was continued at −35° C. After 30 min, additional sodium hydride (27 mg, 0.40 mmol) and 2,2,2-trifluoroethyl trichloromethanesulfonate (0.140 mL, 0.85 mmol) were added. After 2 h, the reaction was quenched with H$_2$O and the mixture was extracted with EtOAc. The organic layer was washed with water (3×), then brine, then dried over MgSO$_4$, filtered and concentrated in vacuo. The residue was purified by silica gel chromatography, eluting with a gradient of hexane:EtOAc—100:0 to 70:30, to give the title compound. MS: m/z=423 (M+1).

Step G: (3R,6S)-3-Amino-6-(2,3-difluorophenyl)-1-(2,2,2-trifluoroethyl)azepan-2-one To a solution of tert-butyl (3R,6S)-6-(2,3-difluorophenyl)-2-oxo-1-(2,2,2-trifluoroethyl)azepan-3-ylcarbamate from Step F (135 mg, 0.320 mmol) in CH$_2$Cl$_2$ (5 mL) was added CF$_3$CO$_2$H (2.5 mL). After 30 min, the solution was concentrated in vacuo and azeotroped with toluene (2×). Saturated aqueous NaHCO$_3$ was added and the mixture was extracted with CH$_2$Cl$_2$ (3×). The combined organic extracts were washed with brine, dried over MgSO$_4$, filtered and concentrated in vacuo to give the title compound. MS: m/z=323 (M+1).

INTERMEDIATE 5

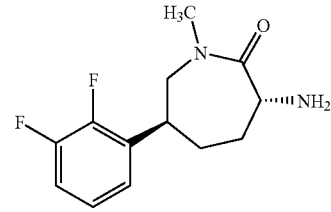 [SMILES: CN1C[C@H](c2cccc(F)c2F)CC[C@@H](N)C1=O]

(3R,6S)-3-Amino-6-(2,3-difluorophenyl)-1-methylazepan-2-one

Essentially following the procedures outlined for the preparation of Intermediate 4, but using iodomethane in place of 2,2,2-trifluoroethyl trichloromethanesulfonate, the title compound was prepared. MS: m/z=255 (M+1).

INTERMEDIATE 6

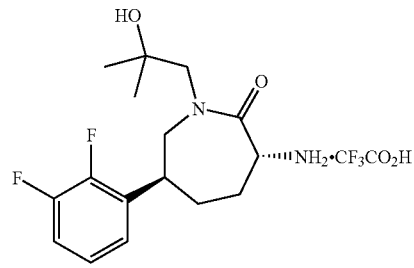

(3R,6S)-3-Amino-6-(2,3-difluorophenyl)-1-(2-hydroxy-2-methylpropyl)azepan-2-one, trifluoroacetic acid salt Step A. Di-tert-butyl [(3R,6S)-6-(2,3-difluorophenyl)-1-(2-hydroxy-2-methylpropyl)-2-oxoazepan-3-yl]imidodicarbonate A mixture of (5S) —$N^2,N^2$-bis(tert-butoxycarbonyl)-5-(2,3-difluorophenyl)-D-lysine (0.569 g, 1.24 mmol, described in Intermediate 4), 1-chloro-2-methyl-2-propanol (0.202 g, 1.86 mmol) and N,N-diisopropylethylamine (0.713 mL, 4.10 mmol) in EtOH (5 mL) was heated at 75° C. for 18 h. The reaction mixture was concentrated to dryness under reduced pressure and the residue was dissolved in $CH_2Cl_2$ (20 mL), then EDC (0.358 g, 1.87 mmol), HOAT (0.252 g, 1.87 mmol) and N,N-diisopropylethylamine (0.650 mL, 3.73 mmol) were added. The resulting mixture was stirred at ambient temperature for 18 h, then aqueous $NaHCO_3$ was added. The layers were separated and the aqueous phase was extracted with $CH_2Cl_2$. The combined organic extracts were dried over $MgSO_4$, filtered, and concentrated in vacuo. The residue was purified by silica gel chromatography, eluting with a gradient of hexane:EtOAc—90:10 to 65:35, to give the title compound. MS: m/z=513 (M+1).

Step B. (3R,6S)-3-Amino-6-(2,3-difluorophenyl)-1-(2-hydroxy-2-methylpropyl)azepan-2-one, trifluoroacetic acid salt To a solution of di-tert-butyl [(3R,6S)-6-(2,3-difluorophenyl)-1-(2-hydroxy-2-methylpropyl)-2-oxoazepan-3-yl]imidodicarbonate from Step A (0.095 g, 0.185 mmol) in $CH_2Cl_2$ (10 mL) was added $CF_3CO_2H$ (3 mL). After 1 h, the solution was concentrated in vacuo to give the title compound. MS: m/z=313 (M+1).

INTERMEDIATE 7

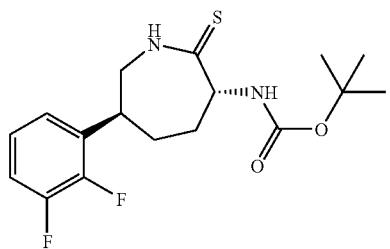 [SMILES: CC(C)(C)OC(=O)N[C@@H]1CC[C@@H](c2cccc(F)c2F)CNC1=S]

tert-Butyl (3R,6S)-6-(2,3-difluorophenyl)-2-thioxoazepan-3-ylcarbamate

Lawesson's reagent [2,4-bis(4-methoxyphenyl)-1,3-dithia-2,4-diphosphetane-2,4-disulfide] (2.90 g, 7.18 mmol) was added to a suspension of tert-butyl (3R,6S)-6-(2,3-difluorophenyl)-2-oxoazepan-3-ylcarbamate (4.79 g, 14.1 mmol, described in Intermediate 4) in toluene (250 mL) and the mixture was heated to 90° C. After 1 h, the reaction was allowed to cool to ambient temperature and concentrated under reduced pressure. The residue was partially purified by silica gel chromatography, eluting with a gradient of $CH_2Cl_2$:EtOAc—100:0 to 85:15.

Further purification by silica gel chromatography, eluting with a gradient of hexane:EtOAc—80:20 to 70:30 afforded the title compound. MS: m/z=357 (M+1).

INTERMEDIATE 8

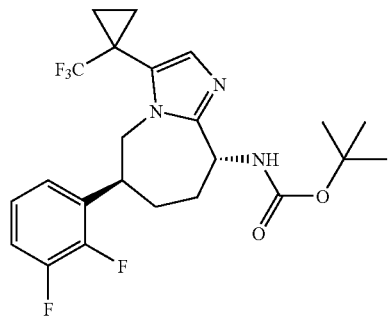 [SMILES: CC(C)(C)OC(=O)N[C@@H]1CC[C@@H](c2cccc(F)c2F)Cn2c(C3(C(F)(F)F)CC3)cnc21]

tert-Butyl {(6S,9R)-6-(2,3-difluorophenyl)-3-[1-(trifluoromethyl)cyclopropyl]-6,7,8,9-tetrahydro-5H-imidazo[1,2-a]azepin-9-yl}carbamate Step A: tert-Butyl [(2Z,3R,6S)-6-(2,3-difluorophenyl)-2-({2-hydroxy-2-[1-(trifluoromethyl)cyclopropyl]ethyl}imino)azepan-3-yl]carbamate Mercury(II) chloride (149 mg, 0.547 mmol) was added to a solution of tert-butyl [(3R,6S)-6-(2,3-difluorophenyl)-2-thioxoazepan-3-yl]carbamate (150 mg, 0.421 mmol, described in Intermediate 7), and 2-amino-1-[1-(trifluoromethyl)cyclopropyl]ethanol (569 mg, 3.367 mmol) in ethanol (5 mL) at 60° C. After 10 min, the reaction was allowed to cool to ambient temperature. The mixture was filtered and concentrated under reduced pressure. Saturated aqueous $NaHCO_3$ was added and the mixture was extracted with $CH_2Cl_2$ (3×). The combined organic extracts were dried over $MgSO_4$, filtered, and concentrated under reduced pressure to give the title compound. MS: m/z=492 (M+1).

Step B: tert-Butyl {(6S,9R)-6-(2,3-difluorophenyl)-3-[1-(trifluoromethyl)cyclopronyl]-6,7,8,9-tetrahydro-5H-imidazo[1,2-a]azepin-9-yl}carbamate Pyridinium dichromate (765 mg, 2.035 mmol) was added to a solution of crude tert-butyl [(2Z,3R,6S)-6-(2,3-difluorophenyl)-2-({2-hydroxy-2-[1-(trifluoromethyl)cyclopropyl]ethyl}imino)azepan-3-yl]carbamate from Step A (200 mg, 0.407 mmol) in acetonitrile (5 mL). After 70 h at ambient temperature, the mixture was filtered and concentrated. Saturated aqueous $NaHCO_3$ was added and the mixture was extracted with $CH_2Cl_2$ (3×). The combined organic extracts were dried over $MgSO_4$, filtered, and concentrated under reduced pressure to give the title compound. MS: m/z=472 (M+1).

INTERMEDIATES 9-10

Essentially following the procedures outlined for Intermediate 2, the compounds listed in Table 1 were prepared. The requisite starting materials were commercially available, described in the literature, synthesized according to methodology described herein, or readily synthesized by one skilled in the art of organic synthesis.

TABLE 1

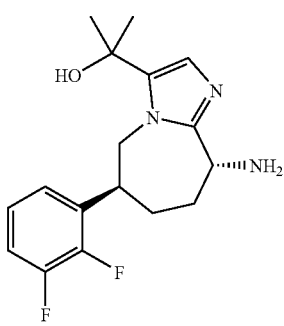 [SMILES: CC(C)(O)c1cnc2n1C[C@H](c1cccc(F)c1F)CC[C@H]2N]

| Intermediate | R¹ | R² | MS (M + 1) |
|---|---|---|---|
| 9 | (isobutyl group) | H | 392 |
| 10 | (methoxy-dimethyl group) | H | 436 |

INTERMEDIATE 11

2-[(6S,9R)-9-Amino-6-(2,3-difluorophenyl)-6,7,8,9-tetrahydro-5H-imidazo[1,2-a]azepin-3-yl]propan-2-ol Concentrated sulfuric acid (0.335 mL, 5.70 mmol) was added to a solution of tert-butyl [(6S,9R)-6-(2,3-difluorophenyl)-3-(1-methoxy-1-methylethyl)-6,7,8,9-tetrahydro-5H-imidazo[1,2-a]azepin-9-yl]carbamate (310 mg, 0.712 mmol) in H₂O (2 mL) and the mixture heated to 60° C. After 2.5 h, the reaction mixture was quenched with saturated aqueous NaHCO₃. The mixture was extracted with CH₂Cl₂ (3×), and the combined organic extracts were washed with water, saturated brine, dried over Na₂SO₄, filtered and concentrated under reduced pressure to give the title compound. MS: m/z=322 (M+1).

INTERMEDIATE 12

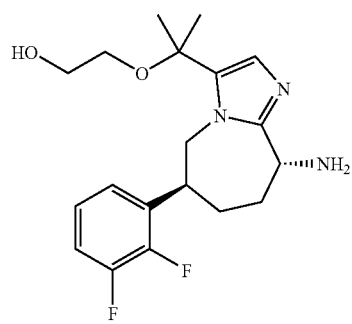 [SMILES: CC(C)(OCCO)c1cnc2n1C[C@H](c1cccc(F)c1F)CC[C@H]2N]

2-{1-[(6S,9R)-9-Amino-6-(2,3-difluorophenyl)-6,7,8,9-tetrahydro-5H-imidazo[1,2-a]azepin-3-yl]-1-methylethoxy}ethanol Essentially following the procedures outlined for the preparation of Intermediate 11, but using ethylene glycol in place of H₂O, the title compound was obtained. MS: m/z=366 (M+1).

INTERMEDIATE 13

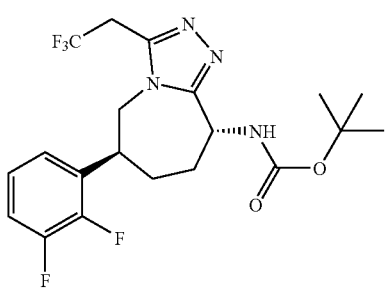 [SMILES: CC(C)(C)OC(=O)N[C@@H]1CC[C@@H](c2cccc(F)c2F)Cn2c(CC(F)(F)F)nnc21]

tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate

Step A: tert-Butyl (3R,6S)-6-(2,3-difluorophenyl)-2-hydrazonoazepan-3-ylcarbamate Hydrazine monohydrate (2.23 mL, 46.0 mmol) was added to a solution of tert-butyl (3R,6S)-6-(2,3-difluorophenyl)-2-thioxoazepan-3-ylcarbamate (546 mg, 1.53 mmol) in methanol (25 mL). After 30 min, the mixture was concentrated under reduced pressure. Saturated aqueous NaHCO$_3$ was added and the mixture was extracted with CH$_2$Cl$_2$ (3×). The combined organic extracts were dried over Na$_2$SO$_4$, filtered, and concentrated under reduced pressure to give the title compound. MS: m/z=355 (M+1).

Step B: tert-Butyl (6S,9R)-6-(2,3-difluorophenyl)-3-(2,2,2-trifluoroethyl)-6,7,8,9-tetrahydro-5H-[1,2,4]triazolo[4,3-a]azepin-9-ylcarbamate Triethylamine (0.259 mL, 1.86 mmol) was added to a solution of tert-butyl (3R,6S)-6-(2,3-difluorophenyl)-2-hydrazonoazepan-3-ylcarbamate from Step A (548 mg, 1.55 mmol), 3,3,3-trifluoropropionic acid (0.205 mL, 2.32 mmol), EDC (356 mg, 1.86 mmol), and 1-hydroxy-7-azabenzotriazole (253 mg, 1.86 mmol) in dichloromethane (55 mL). After 18 h, saturated aqueous NaHCO$_3$ was added and the mixture was extracted with CH$_2$Cl$_2$ (3×). The combined organic extracts were dried over Na$_2$SO$_4$, filtered, and concentrated under reduced pressure. The residue was purified by silica gel chromatography, eluting with a gradient of CH$_2$Cl$_2$:MeOH—100:0 to 96:4, to give the title compound. MS: m/z=447 (M+1).

INTERMEDIATES 14-15

Essentially following the procedures outlined for Intermediate 13, the compounds listed in Table 2 were prepared. The requisite starting materials were commercially available, described in the literature, synthesized according to methodology described herein, or readily synthesized by one skilled in the art of organic synthesis.

TABLE 2

| Intermediate | R | MS (M + 1) |
|---|---|---|
| 14 | (cyclopropyl with CF$_3$) | 473 |
| 15 | 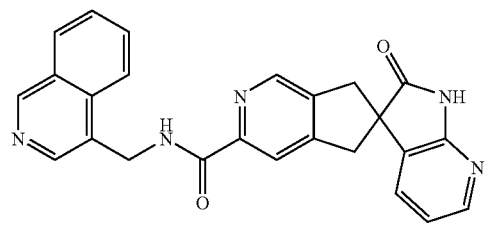 | 423 |

EXAMPLE 1

N-(Isoquinolin-4-ylmethyl)-2'-oxo-1',2',5,7-tetrahydrospiro[cyclopenta[c]pyridine-6,3'-pyrrolo[2,3-b]pyridine]-3-carboxamide A mixture of (isoquinolin-4-ylmethyl)amine dihydrochloride (20 mg, 0.087 mmol), (±)-2'-oxo-1',2',5,7-tetrahydrospiro[cyclopenta[c]pyridine-6,3'-pyrrolo[2,3-b]pyridine]-3-carboxylic acid hydrochloride (28 mg, 0.087 mmol, described in Intermediate 2), EDC (25 mg, 0.130 mmol), HOBT (20 mg, 0.130 mmol), and N,N-diisopropylethylamine (0.060 mL, 0.346 mmol) was stirred in DMF (0.5 mL) at ambient temperature for 18 h. The reaction mixture was purified directly by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated in vacuo to provide the title compound as the TFA salt. MS: m/z=422 (M+1). HRMS: m/z=422.1621; calculated m/z=422.1612 for C$_{25}$H$_{20}$N$_5$O$_2$.

EXAMPLES 2-42

Essentially following the procedures outlined for Example 1, the compounds listed in Table 3 were prepared. The requisite amines were commercially available, described in the literature, synthesized according to methodology described herein, or readily synthesized by one skilled in the art of organic synthesis. In some cases, straightforward protecting group strategies were applied.

TABLE 3
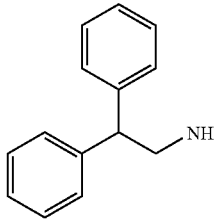 [SMILES: NCC(c1ccccc1)c1ccccc1]
| Example | $R^a$ | MS (M + 1) |
|---|---|---|
| 2 | 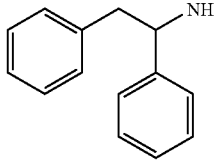 | 461 |
| 3 | 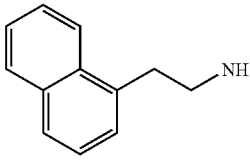 | 461 |
| 4 | 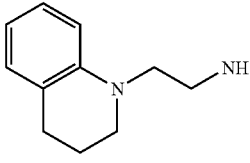 | 435 |
| 5 | 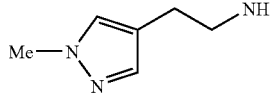 | 440 |
| 6 | 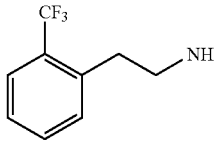 | 389 |
| 7 | 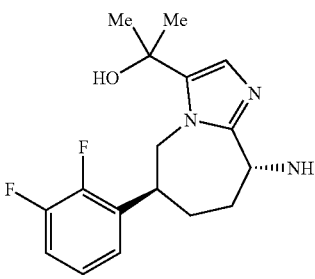 | 453 |
| 8 |  | 585 |

TABLE 3-continued
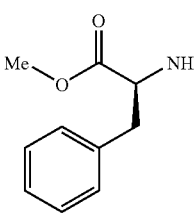 [SMILES: COC(=O)[C@@H](N)Cc1ccccc1]
| Example | R$^a$ | MS (M + 1) |
|---|---|---|
| 9 | 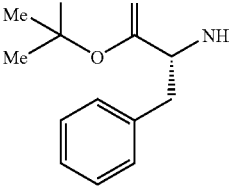 | 443 |
| 10 | 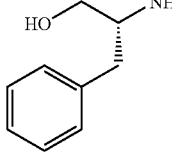 | 485 |
| 11 | 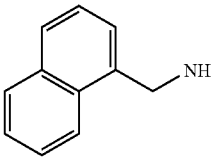 | 415 |
| 12 | 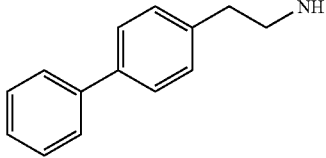 | 421 |
| 13 | 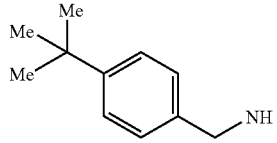 | 461 |
| 14 | 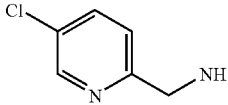 | 427 |
| 15 | | 406 |

TABLE 3-continued
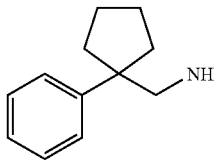 [SMILES: NCC1(c2ccccc2)CCCC1]
| Example | Rª | MS (M + 1) |
|---|---|---|
| 16 | 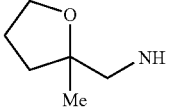 | 439 |
| 17 | 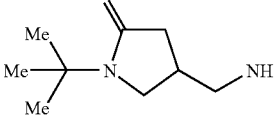 | 379 |
| 18 | 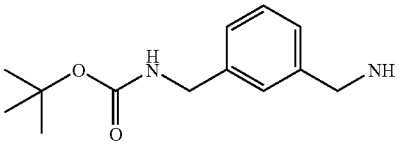 | 434 |
| 19 | 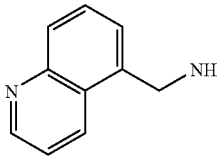 | 500 |
| 20 | 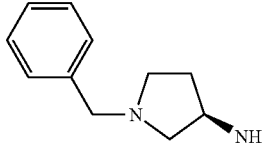 | 422 |
| 21 | 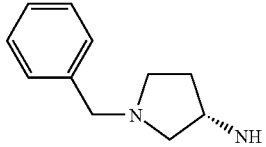 | 440 |
| 22 | 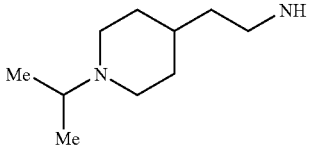 | 440 |
| 23 | 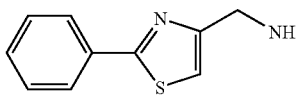 | 434 |
| 24 | | 454 |

TABLE 3-continued

| Example | R^a | MS (M + 1) |
|---|---|---|
| 25 | *1-methyl-4-phenylpiperidin-4-yl-methylamine* | 468 |
| 26 | *1-(thiophen-2-yl)propan-2-ylamine* | 405 |
| 27 | *2-amino-1-(1H-indol-3-yl)ethanone* | 438 |
| 28 | *(2-(1H-1,2,4-triazol-1-yl)phenyl)methylamine* | 438 |
| 29 | *2-(4-(4-methylphenethyl)piperidin-1-yl)ethylamine* | 510 |
| 30 | *2-(3,4-dihydroisoquinolin-2(1H)-yl)ethylamine* | 440 |
| 31 | *2-(4-(o-tolyl)piperazin-1-yl)ethylamine* | 483 |
| 32 | *benzylamine* | 371 |

TABLE 3-continued

| Example | R$^a$ | MS (M + 1) |
| --- | --- | --- |
| 33 | phenethylamino | 385 |
| 34 | tert-butyl 3-aminopyrrolidine-1-carboxylate | 450 |
| 35 | (3-phenylisoxazol-5-yl)methylamino | 438 |
| 36 | 2-(4-benzylpiperazin-1-yl)ethylamino | 483 |
| 37 | (pyrimidin-4-yl)methylamino | 373 |
| 38 | 2,2,2-trifluoro-1-phenylethylamino | 439 |
| 39 | (4-(isoxazol-3-yl)phenyl)methylamino | 438 |
| 40 | 1-amino-spiro[indane-2,4'-piperidine] | 466 |
| 41 | (5-phenylpyrrolidin-3-yl)methylamino | 440 |

TABLE 3-continued

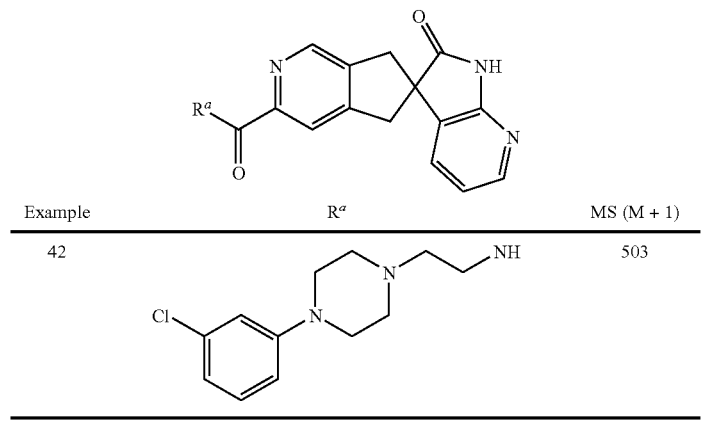

| Example | R$^a$ | MS (M + 1) |
|---|---|---|
| 42 | 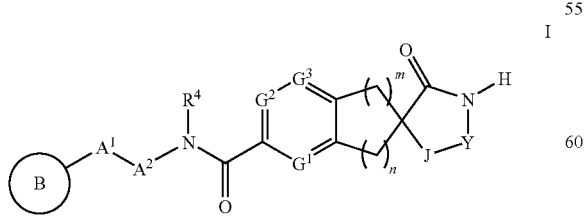 | 503 |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diasteriomer subsequent to a chiral resolution) will provide alternative enantiomers and diastereomers, all of which are included in the spirit and scope of the invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of formula I:

I wherein:
B is selected from the group consisting of phenyl, thienyl, pyridinyl, isoquinolinyl, tetrahydroisoquinolinyl, naphthyl, isoxazolyl, indolyl, piperidinyl, tetrahydrofuranyl, piperazinyl, pyrazolyl and pyrrolidinyl (which is optionally substituted with oxo), wherein B is unsubstituted or substituted with 1-5 substituents each independently selected from $R^1$, $R^2$, $R^{3a}$ and $R^{3b}$;

$R^1$, $R^2$, $R^{3a}$ and $R^{3b}$ are independently selected from:
(1) —$C_{1-6}$alkyl, which is unsubstituted or substituted with 1-7 substituents each independently selected from:
  (a) halo,
  (b) hydroxy,
  (c) —O—$C_{1-6}$alkyl,
  (d) —$C_{3-6}$cycloalkyl,
  (e) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl,
    and wherein said phenyl or heterocycle is unsubstituted or substituted with 1-5 substituents each independently selected from
    (i) —$C_{1-6}$alkyl,
    (ii) —O—$C_{1-6}$alkyl,
    (iii) halo,
    (iv) hydroxy,
    (v) trifluoromethyl, and
    (vi) —$OCF_3$,
  (f) —$CO_2R^9$, wherein $R^9$ is selected from
    (i) hydrogen,
    (ii) —$C_{1-6}$alkyl which is unsubstituted or substituted with 1-6 fluoro,
    (iii) —$C_{5-6}$cycloalkyl,
    (iv) benzyl and
    (v) phenyl,
  (g) —$NR^{10}R^{11}$, wherein $R^{10}$ and $R^{11}$ are each independently selected from:
    (i) hydrogen,
    (ii) —$C_{1-6}$alkyl which is unsubstituted or substituted with 1-6 fluoro,
    (iii) —$C_{5-6}$cycloalkyl,
    (iv) benzyl,
    (v) phenyl,
    (vi) —$CO_2R^9$ and
    (vii) —$SO_2R^{12}$, wherein $R^{12}$ is: (I) —$C_{1-6}$alkyl which is unsubstituted or substituted with 1-6 fluoro; (II) —$C_{5-6}$cycloalkyl; (III) benzyl; or (IV) phenyl;

(h) —SO$_2$R$^{12}$,
(i) —CONR$^{10a}$R$^{11a}$, wherein:
R$^{10a}$ and R$^{11a}$ are each independently:
(i) hydrogen;
(ii) —C$_{1-6}$alkyl which is unsubstituted or substituted with 1-6 fluoro;
(iii) —C$_{5-6}$cycloalkyl;
(iv) benzyl; or
(v) phenyl; or
R$^{10a}$ and R$^{11a}$ are joined to form a ring selected from azetidinyl, pyrrolidinyl, piperidinyl, piperazinyl and morpholinyl, which ring is unsubstituted or substituted with 1-5 substituents each independently selected from
(i) —C$_{1-6}$ alkyl;
(ii) —O—C$_{1-6}$ alkyl;
(iii) halo;
(iv) hydroxyl;
(v) phenyl; or
(vi) benzyl;
(j) trifluoromethyl,
(k) —OCO$_2$R$^9$,
(l) —(NR$^{10a}$)CO$_2$R$^9$,
(m) —O(CO)NR$^{10a}$R$^{11a}$; or
(n) —(NR$^9$)(CO)NR$^{10a}$R$^{11a}$;
(2) —C$_{3-6}$cycloalkyl, which is unsubstituted or substituted with 1-7 substituents each independently selected from
(a) halo,
(b) hydroxy,
(c) —O—C$_{1-6}$ alkyl,
(d) trifluoromethyl and
(e) phenyl, wherein the phenyl is unsubstituted or substituted with 1-5 substituents each independently selected from
(i) —C$_{1-6}$ alkyl,
(ii) —O—C$_{1-6}$ alkyl,
(iii) halo,
(iv) hydroxy and
(v) trifluoromethyl,
(3) phenyl or heterocycle, wherein the heterocycle is selected from pyridinyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, benzimidazolyl, benzopyranyl, benzofuryl, benzothiazolyl, benzoxazolyl, chromanyl, furyl, imidazolidinyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, and wherein the phenyl or heterocycle is unsubstituted or substituted with 1-5 substituents each independently selected from:
(a) —C$_{1-6}$alkyl which is unsubstituted or substituted with 1-6 fluoro,
(b) halo,
(c) hydroxy,
(d) —O—C$_{1-6}$alkyl, which is unsubstituted or substituted with 1-6 fluoro,
(e) —C$_{3-6}$cycloalkyl,
(f) phenyl or heterocycle, wherein the heterocycle is selected from pyridinyl, pyrimidinyl, pyrazinyl, thienyl and morpholinyl,
and wherein the phenyl or heterocycle is unsubstituted or substituted with 1-5 substituents each independently selected from
(i) —C$_{1-6}$ alkyl,
(ii) —O—C$_{1-6}$ alkyl,
(iii) halo,
(iv) hydroxy and
(v) trifluoromethyl,
(g) —CO$_2$R$^9$,
(h) —NR$^{10}$R$^{11}$,
(i) —CONR$^{10}$R$^{11}$,
(j) —SO$_2$R$^{12}$, and
(k) oxo,
(4) halo,
(5) oxo,
(6) hydroxy,
(7) —O—C$_{1-6}$alkyl, which is unsubstituted or substituted with 1-5 halo,
(8) —CN,
(9) —CO$_2$R$^9$,
(10) —NR$^{10}$R$^{11}$,
(11) —SO$_2$R$^{12}$,
(12) —CONR$^{10a}$R$^{11a}$,
(13) —OCO$_2$R$^9$,
(14) —(NR$^{10a}$)CO$_2$R$^9$,
(15) —O(CO)NR$^{10a}$R$^{11a}$,
(16) —(NR$^9$)(CO)NR$^{10a}$R$^{11a}$,
(17) —SO$_2$NR$^{10a}$R$^{11a}$,
(18) —SR$^{12}$,
(19) —S(O)R$^{12}$,
(20) —(NR$^9$)(CO)NR$^{10a}$R$^{11a}$,
(21) —(CO)—(CO)NR$^{10a}$R$^{11a}$, and
(22) —(CO)—(CO)OR$^9$;
or R$^{3a}$ and R$^{3b}$ and the atom(s) to which they are attached are joined to form a ring selected from azetidinyl, azepanyl, azepinyl, cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, thiadiazolyl, oxadiazolyl, isoxazolyl, pyrazolyl, triazolyl, pyridinyl, pyrimidinyl, pyrazinyl, pyridazinyl, triazinyl, pyrrolyl, pyrrolinyl, morpholinyl, azetidinyl, pyrrolidinyl, piperidinyl, tetrahydrofuranyl, tetrahydropyranyl, tetrahydropyridinyl, furanyl, dihydrofuranyl, dihydropyranyl, dihydrothienyl, tetrahydrothienyl, dihydrothiopyranyl, tetrahydrothiopyranyl, pyrrolidinyl, piperidinyl, and piperazinyl, which ring is unsubstituted or substituted with 1-5 substituents each independently selected from:
(a) —C$_{1-6}$alkyl, which is unsubstituted or substituted with 1-3 substituents each independently selected from:
(i) halo,
(ii) hydroxy,
(iii) —O—C$_{1-6}$alkyl, which is unsubstituted or substituted with 1-5 substituents each independently selected from
(I) —O—C$_{1-6}$alkyl,
(II) halo, and
(III) hydroxy,
(iv) —C$_{3-6}$cycloalkyl, which is unsubstituted or substituted with 1-5 substituents each independently selected from
(I) —C$_{1-6}$alkyl,
(II) —O—C$_{1-6}$alkyl,
(III) halo,
(IV) hydroxy, (V) trifluoromethyl and
(VI) —OCF$_3$,
(v) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from
(I) —C$_{1-6}$alkyl,
(II) —O—C$_{1-6}$alkyl,
(III) halo,
(IV) hydroxy,
(V) trifluoromethyl and
(VI) —OCF$_3$,
(vi) —CO$_2$R$^9$,
(vii) —NR$^{10}$R$^{11}$,
(viii) —SO$_2$R$^{12}$,
(ix) —CONR$^{10a}$R$^{11a}$, and
(x) —(NR$^{10a}$)CO$_2$R$^9$,
(b) —C$_{3-6}$cycloalkyl, which is unsubstituted or substituted with 1-5 substituents each independently selected from
(i) halo,
(ii) hydroxy,
(iii) —O—C$_{1-6}$alkyl,
(iv) trifluoromethyl and
(v) phenyl,
(c) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
(i) halo,
(ii) hydroxy,
(iii) —C$_{3-6}$cycloalkyl,
(iv) —O—C$_{1-6}$alkyl which is unsubstituted or substituted with 1-6 fluoro, and
(v) —C$_{1-6}$alkyl which is unsubstituted or substituted with 1-6 fluoro,
(d) halo,
(e) —SO$_2$R$^{12}$,
(f) hydroxy,
(g) —O—C$_{1-6}$alkyl which is unsubstituted or substituted with 1-5 halo,
(h) —CN,
(i) —COR$^{12}$,
(j) —NR$^{10}$R$^{11}$,
(k) —CONR$^{10a}$R$^{11a}$,
(l) —CO$_2$R$^9$,
(m) —(NR$^{10a}$)CO$_2$R$^9$,
(n) —O(CO)NR$^{10a}$R$^{11a}$,
(o) —(NR$^9$)(CO)NR$^{10a}$R$^{11a}$, and
(p) oxo;
A$^1$ and A$^2$ are each independently selected from:
(1) a bond,
(2) —CR$^{13}$R$^{14}$—, wherein R$^{13}$ and R$^{14}$ are independently selected from
(a) hydrogen,
(b) C$_{1-6}$ alkyl, which is unsubstituted or substituted with 1-5 substituents each independently selected from
(i) halo,
(ii) hydroxy,
(iii) —NR$^{10}$R$^{11}$,
(iv) —CONR$^{10a}$R$^{11a}$ and
(v) —CO$_2$R$^9$,
(c) phenyl, which is unsubstituted or substituted with 1-3 substituents each independently selected from
(i) C$_{1-4}$alkyl,
(ii) hydroxyl and
(iii) halo,
(d) —CONR$^{10}$—(C$_{1-6}$alkyl)-NR$^{15a}$R$^{16a}$, wherein R$^{15a}$ and R$^{16a}$ are each independently selected from
(i) hydrogen,
(ii) —C$_{1-6}$ alkyl,
(iii) —COR$^9$ and
(iv) —CO$_2$R$^9$,
(e) —CO$_2$R$^9$,
(f) —CONR$^{10a}$R$^{11a}$, and
(g) hydroxy, or
(3) —CH$_2$CR$^{13}$R$^{14}$—, and
(4) —C(=O)—;
G$^1$ and G$^3$ are each —C(R$^5$)=,
G$^2$ is —N= or -(N$^{+-O-}$)=;
J is independently selected from:
(1) =C(R$^{6a}$)—,
(2) —CR$^{13}$R$^{14}$—,
(3) —C(=O)—, and
(4) —N(R$^{15}$)—;
Y is independently selected from:
(1) =C(R$^{6b}$)—,
(2) —CR$^{13}$R$^{14}$—,
(3) —C(=O)—,
(4) —SO$_2$—,
(5) =N—, and
(6) —N(R$^{6b}$)—;
R$^4$ is selected from
(1) hydrogen,
(2) C$_{1-6}$ alkyl which is unsubstituted or substituted with 1-6 fluoro,
(3) C$_{5-6}$ cycloalkyl,
(4) benzyl and
(5) phenyl,
or R$^4$ is joined to B to form a ring selected from piperidinyl, pyrrolidinyl, piperazinyl, azetidinyl, azepinyl and morpholinyl, which ring is unsubstituted or substituted with 1-5 substituents each independently selected from
(1) —C$_{1-6}$ alkyl,
(2) —O—C$_{1-6}$alkyl,
(3) halo,
(4) hydroxy,
(5) phenyl and
(6) benzyl;
R$^5$ is independently selected from:
(1) hydrogen,
(2) C$_{1-6}$ alkyl,
(3) —O—C$_{1-6}$alkyl,
(4) —OCF$_3$,
(5) trifluoromethyl,
(6) halo,
(7) hydroxy, and
(8) —CN;
R$^{6a}$ and R$^{6b}$ are each independently selected from:
(1) hydrogen;
(2) —C$_{1-4}$alkyl, which is unsubstituted or substituted with 1-5 substituents each independently selected from:
(a) halo,
(b) —O—C$_{1-6}$alkyl,
(c) —C$_{3-6}$cycloalkyl,
(d) phenyl or heterocycle, wherein the heterocycle is selected from imidazolyl, oxazolyl, pyridinyl, pyrimidinyl, pyrazinyl, pyridazinyl, piperidinyl, piperazinyl, pyrrolidinyl, thiazolyl, thienyl, triazolyl, or morpholinyl, which phenyl or heterocycle is unsubstituted or substituted with 1-3 substituents each independently selected from
(i) —$C_{1-6}$alkyl,
(ii) —O—$C_{1-6}$ alkyl,
(iii) halo,
(iv) hydroxy,
(v) trifluoromethyl and
(vi) —$OCF_3$,
(3) phenyl or heterocycle, wherein the heterocycle is selected from pyridinyl, pyrimidinyl, pyrazinyl, thienyl, pyrrolidinyl, azetidinyl, thiazolyl, oxazolyl, imidazolyl, triazolyl, tetrahydrofuryl, piperidinyl, and morpholinyl, which phenyl or heterocycle is unsubstituted or substituted with 1-3 substituents each independently selected from
(a) —$C_{1-4}$alkyl which is unsubstituted or substituted with 1-5 fluoro,
(b) halo,
(c) hydroxy,
(d) —O—$C_{1-4}$alkyl which is unsubstituted or substituted with 1-5 fluoro,
(e) —$C_{3-6}$cycloalkyl and
(f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$,
or $R^{6a}$ and $R^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
(a) —$C_{1-6}$alkyl, which is unsubstituted or substituted with 1-3 substituents each independently selected from:
(i) halo,
(ii) hydroxy,
(iii) —O—$C_{1-6}$ alkyl,
(iv) —$C_{3-6}$cycloalkyl,
(v) phenyl or heterocycle, wherein the heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from
(I) —$C_{1-6}$alkyl,
(II) —O—$C_{1-6}$alkyl,
(III) halo,
(IV) hydroxy,
(V) trifluoromethyl and
(VI) —$OCF_3$,
(vi) —$CO_2R^9$,
(vii) —$NR^{10}R^{11}$,
(viii) —$SO_2R^{12}$,
(ix) —$CONR^{10a}R^{11a}$, and
(x) —$(NR^{10a})CO_2R^9$, (b) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
(i) —$C_{1-6}$alkyl, which is unsubstituted or substituted with 1-6 fluoro,
(ii) —O—$C_{1-6}$alkyl, which is unsubstituted or substituted with 1-6 fluoro,
(iii) halo,
(iv) hydroxy, and
(v) —$C_{3-6}$cycloalkyl,
(c) halo,
(d) —$SO_2R^{12}$,
(e) hydroxy,
(f) —O—$C_{1-6}$alkyl, which is unsubstituted or substituted with 1-5 halo,
(g) —CN,
(h) —$COR^{12}$,
(i) —$NR^{10}R^{11}$,
(j) —$CONR^{10a}R^{11a}$,
(k) —$CO_2R^9$,
(l) —$(NR^{10a})CO_2R^9$,
(m) —$O(CO)NR^{10a}R^{11a}$,
(n) —$(NR^9)(CO)NR^{10a}R^{11a}$, and
(o) oxo;
$R^{15}$ is independently for each occurrence:
(1) hydrogen, or
(2) —$C_{1-4}$alkyl which is unsubstituted or substituted with 1-3 substituents which are independently halo or phenyl;
m is 1;
n is 1;
or a pharmaceutically acceptable salt thereof, individual enantiomer, or diastereomer thereof.

2. A compound of claim 1, wherein $R^1$, $R^2$, $R^{3a}$ and $R^{3b}$ are independently:
(1) $C_{1-6}$ alkyl, which is unsubstituted or substituted with 1-5 halo or hydroxyl;
(2) $C_{3-6}$ cycloalkyl;
(3) —O—$C_{1-6}$alkyl;
(4) —$OCF_3$;
(5) trifluoromethyl;
(6) halo;
(7) oxo;
(8) —CN;
(9) —$COR^{12}$;
(10) —$CO_2R^{12}$;
(11) —$CONR^{10a}R^{11a}$;
(12) —$NR^{10a}CO_2R^9$;
(13) phenyl, which is unsubstituted or substituted with 1-5 substituents each independently selected from: $C_{1-6}$alkyl, —O—$C_{1-6}$alkyl, halo, —OH and —$CF_3$; or
(14) heterocycle selected from: pyridyl, pyrimidinyl, pyrazinyl, thienyl, pyrrolidinyl, piperidinyl or morpholinyl, which is unsubstituted or substituted with 1-5 substituents each independently selected from: $C_{1-6}$alkyl, —O—$C_{1-6}$alkyl, halo, —OH and —$CF_3$,
or a pharmaceutically acceptable salt thereof, individual enantiomer, or diastereomer thereof.

3. A compound of claim 1, wherein $A^1$ is a bond and $A^2$ is —$CH_2$—, or a pharmaceutically acceptable salt thereof, individual enantiomer, or diastereomer thereof.

4. A compound of claim 1, wherein $A^1$ and $A^2$ are both $CR^{13}R^{14}$, wherein $R^{13}$ and $R^{14}$ are independently: (a) hydrogen; or (b) C$_{1-6}$ alkyl, which is unsubstituted or substituted with 1-5 halo or hydroxyl; or a pharmaceutically acceptable salt thereof, individual enantiomer, or diastereomer thereof.

5. A compound of claim 1, wherein A$^1$ is —CH$_2$— or a bond, and A$^2$ is (C=O), or a pharmaceutically acceptable salt thereof, individual enantiomer, or diastereomer thereof.

6. A compound of claim 1, wherein J is =C(R$^{6a}$)—; —CH$_2$—; or —N(R$^{15}$).

7. A compound of claim 1, wherein Y is =C(R$^{6b}$)—; —CH$_2$—; or —C(=O ereof.

8. A compound of claim 1, wherein J is =C(R$^{6a}$)— and Y is =C(R$^{6b}$)—, wherein R$^{6a}$ and R$^{6b}$ and the atom(s) to which they are attached are joined to form a ring selected from cyclopentenyl, cyclohexenyl, phenyl, pyridinyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) hydroxy,
    (iii) —O—C$_{1-6}$alkyl,
    (iv) —C$_{3-6}$cycloalkyl,
    (v) phenyl or heterocycle, wherein the heterocycle is selected from: pyridinyl, pyrimidinyl, pyrazinyl, pyridazinyl, piperidinyl, piperazinyl, pyrrolidinyl, thienyl, or morpholinyl, which is unsubstituted or substituted with 1-5 substituents where the substituents are each independently selected from
      (I) —C$_{1-6}$alkyl,
      (II) —O—C$_{1-6}$alkyl,
      (III) halo,
      (IV) hydroxy,
      (V) trifluoromethyl and
      (VI) —OCF$_3$,
    (vi) —CO$_2$R$^9$,
    (vii) —NR$^{10}$R$^{11}$,
    (viii) —SO$_2$R$^{12}$,
    (ix) —CONR$^{10a}$R$^{11a}$, and
    (x) —(NR$^{10a}$)CO$_2$R$^9$,
  (b) phenyl or heterocycle, wherein the heterocycle is selected from pyridinyl, pyrimidinyl pyrazinyl, thienyl, pyridazinyl, pyrrolidinyl, azetidinyl, piperidinyl and morpholinyl, which phenyl or heterocycle is unsubstituted or substituted with 1-3 substituents each independently selected from
    (i) —C$_{1-6}$alkyl, which is unsubstituted or substituted with 1-6 fluoro,
    (ii) —O—C$_{1-6}$alkyl, which is unsubstituted or substituted with 1-6 fluoro,
    (iii) halo,
    (iv) hydroxy, and
    (v) —C$_{3-6}$cycloalkyl,
  (c) halo,
  (d) —SO$_2$R$^{12}$,
  (e) hydroxy,
  (f) —O—C$_{1-6}$alkyl, which is unsubstituted or substituted with 1-5 halo,
  (g) —CN,
  (h) —COR$^{12}$,
  (i) —NR$^{10}$R$^{11}$,
  (j) —CONR$^{10a}$R$^{11a}$,
  (k) —CO$_2$R$^9$,
  (l) —(NR$^{10a}$)CO$_2$R$^9$,
  (m) —O(CO)NR$^{10a}$R$^{11a}$,
  (n) —(NR$^9$)(CO)NR$^{10a}$R$^{11a}$, and
  (o) oxo, or a pharmaceutically acceptable salt thereof, individual enantiomer, or diastereomer thereof.

9. A compound of claim 1, which is a compound of formula (II):

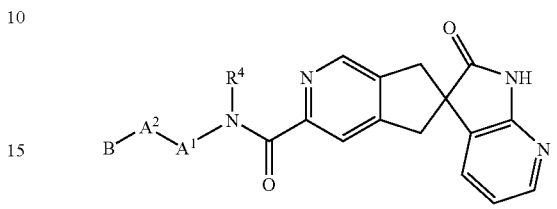

or a pharmaceutically acceptable salt thereof, individual enantiomer, or diastereomer thereof.

10. A compound which is:

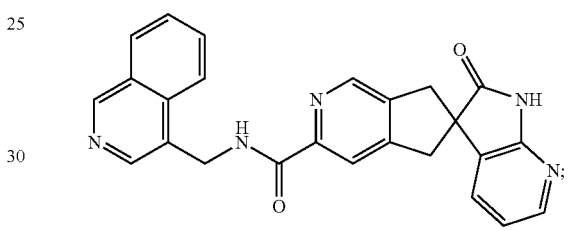

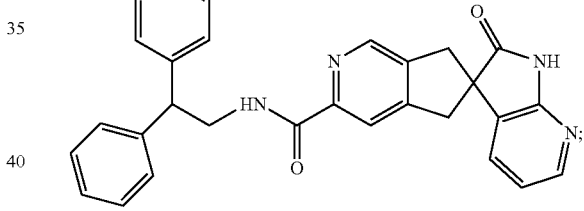

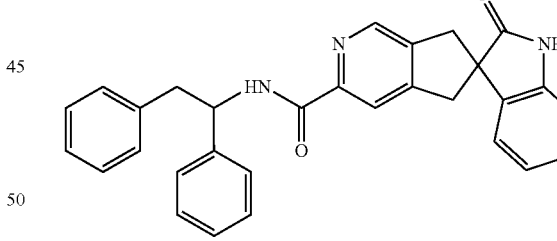

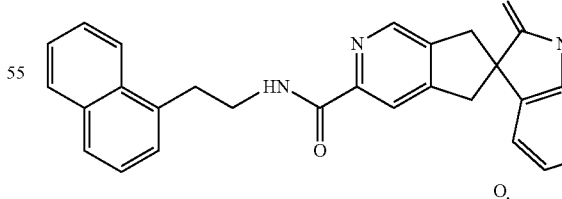

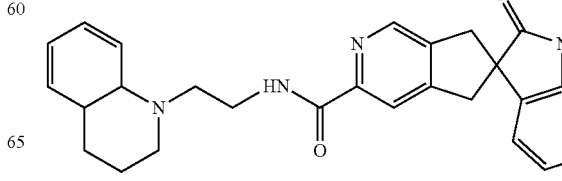

63
-continued
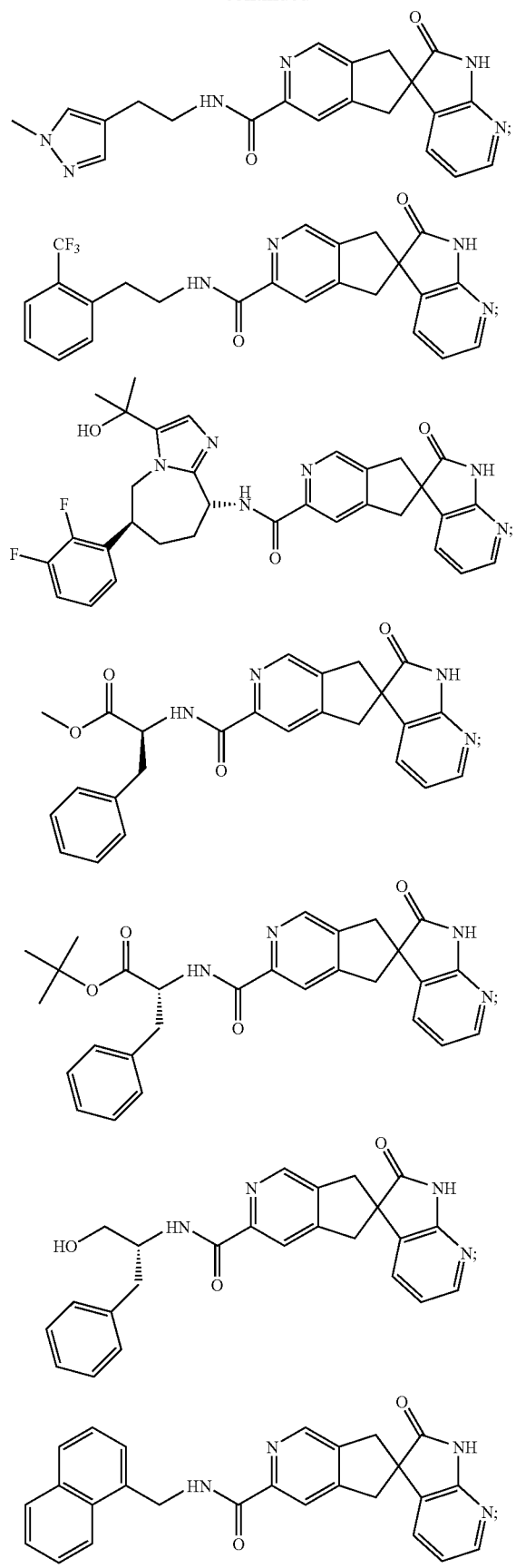
64
-continued
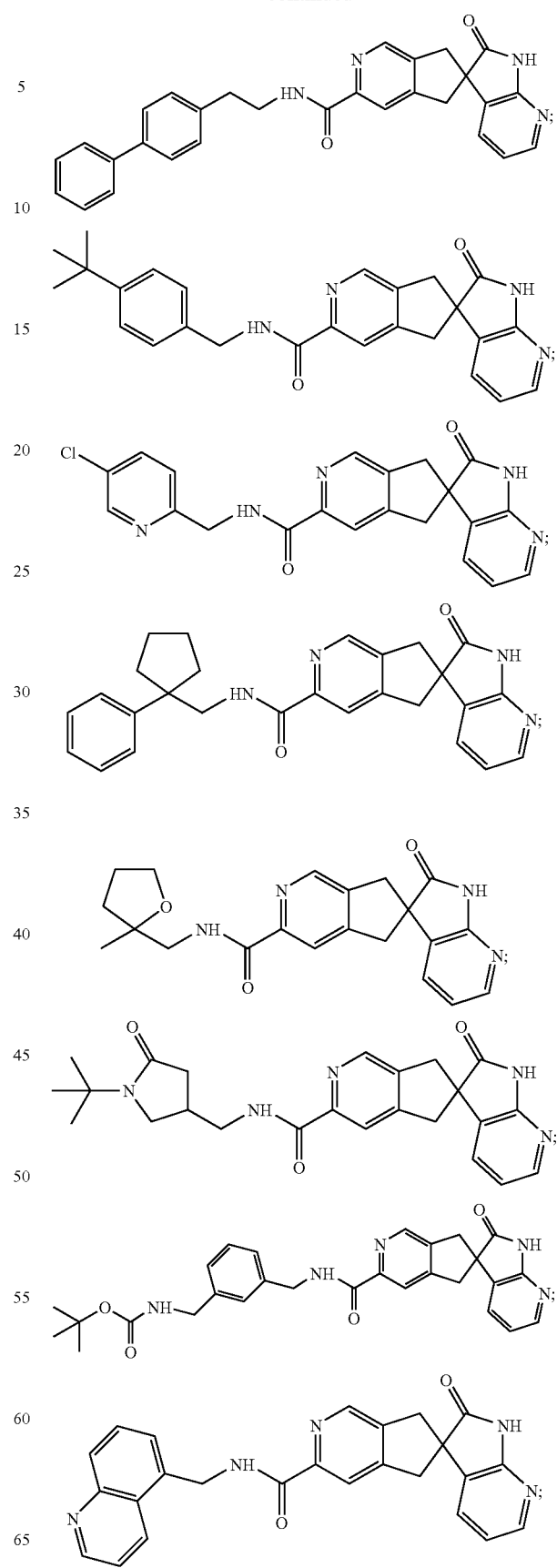

65
-continued
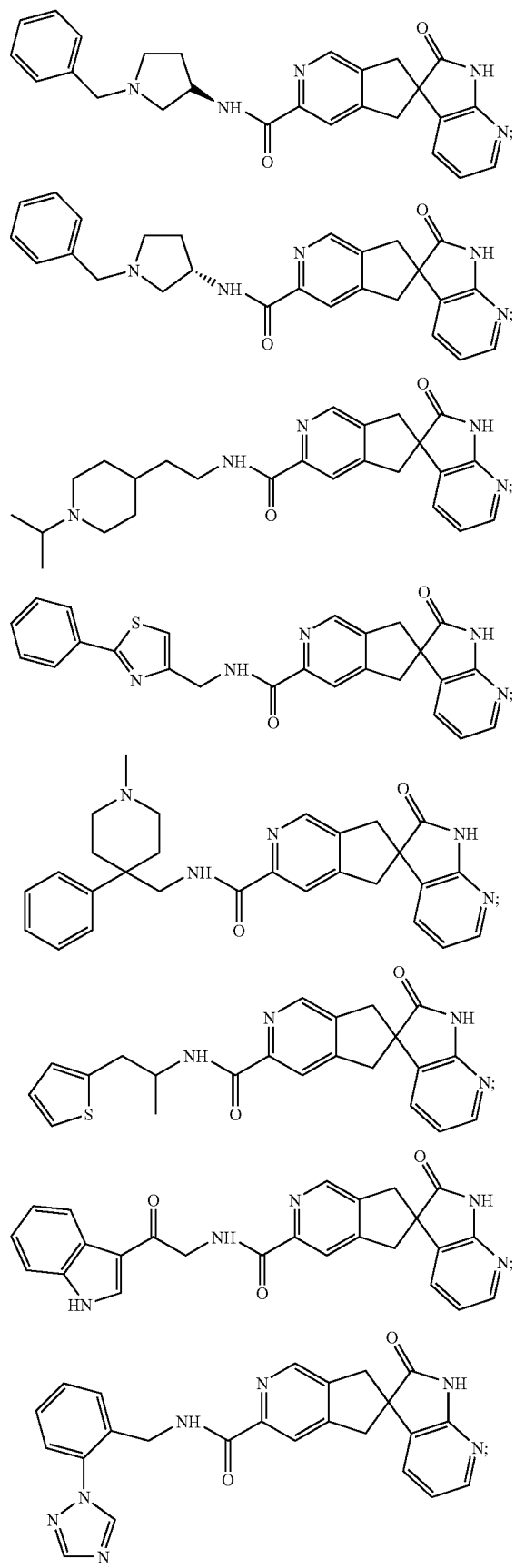
66
-continued
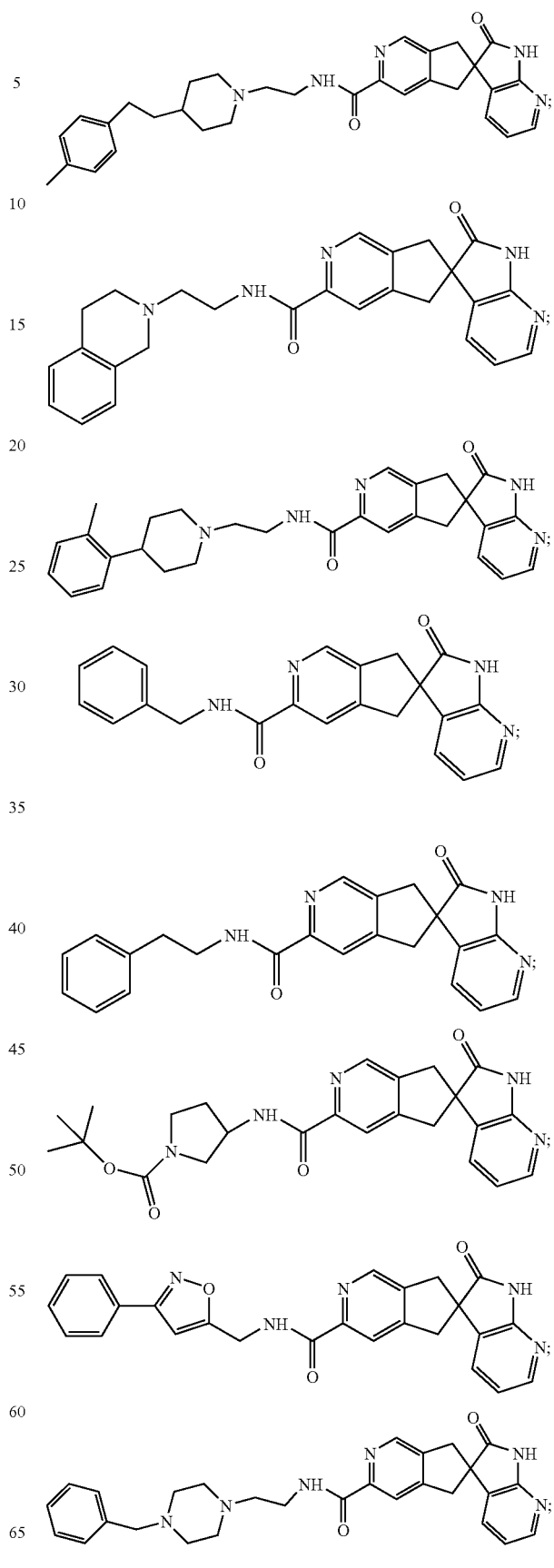

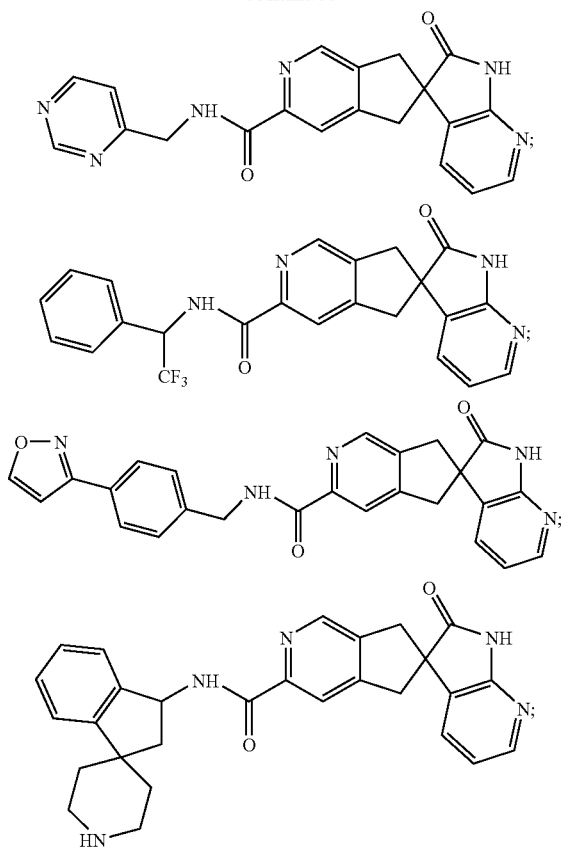

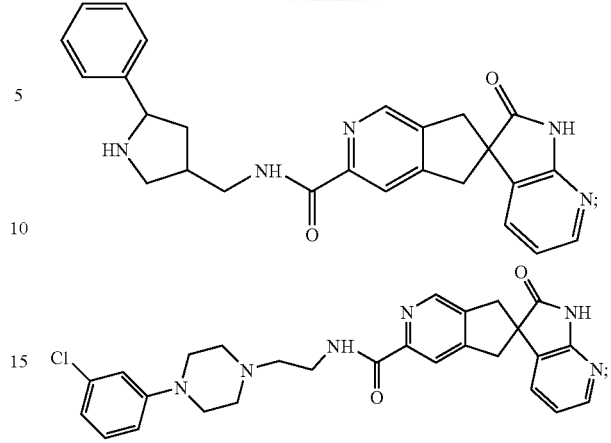

or a pharmaceutically acceptable salt thereof.

11. A pharmaceutical composition comprising a pharmaceutically acceptable carrier and a compound of claim 1 or a pharmaceutically acceptable salt thereof.

12. A method for antagonism of CGRP receptor activity in a mammal which comprises the administration of an effective amount of a compound of claim 1 or a pharmaceutically acceptable salt thereof.

13. A method for treating headache in a mammalian patient in need thereof, which comprises administering to the patient a therapeutically effective amount of a compound of claim 10 or a pharmaceutically acceptable salt thereof.

14. The method of claim 13 wherein the headache is a migraine or a cluster headache.

* * * * *